United States Patent
Harper et al.

(10) Patent No.: US 7,319,004 B2
(45) Date of Patent: Jan. 15, 2008

(54) MATERIALS AND METHODS RELATING TO POLYIONS AND SUBSTANCE DELIVERY

(75) Inventors: Garry R. Harper, Sitting Bourne (GB); Paula Cooper, Canterbury (GB); Matthew J. Baker, Maidstone (GB)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 10/516,203

(22) PCT Filed: Jun. 2, 2003

(86) PCT No.: PCT/GB03/02417

§ 371 (c)(1),
(2), (4) Date: Jan. 9, 2006

(87) PCT Pub. No.: WO03/101494

PCT Pub. Date: Dec. 11, 2003

(65) Prior Publication Data

US 2006/0204584 A1    Sep. 14, 2006

(30) Foreign Application Priority Data

May 31, 2002 (GB) .................. 0212826.2

(51) Int. Cl.
*C12Q 1/68* (2006.01)
(52) U.S. Cl. ........................................ 435/6
(58) Field of Classification Search ............... 435/6, 435/4, 7.1, 7.92; 604/890.1; 436/526, 518
See application file for complete search history.

(56) References Cited

U.S. PATENT DOCUMENTS

| | | | |
|---|---|---|---|
| 4,923,978 A | 5/1990 | McCormick | |
| 4,965,007 A * | 10/1990 | Yudelson | ................. 252/62.53 |
| 5,057,426 A | 10/1991 | Henco et al. | |
| 5,460,831 A | 10/1995 | Kossovsky et al. | |
| 5,679,559 A | 10/1997 | Kim et al. | |
| 5,908,777 A | 6/1999 | Lee et al. | |
| 6,060,246 A | 5/2000 | Summerton et al. | |
| 6,090,288 A | 7/2000 | Berglund et al. | |
| 6,383,811 B2 * | 5/2002 | Wolff et al. | ................. 435/450 |
| 6,562,573 B2 | 5/2003 | Halaka | |

FOREIGN PATENT DOCUMENTS

| | | |
|---|---|---|
| EP | 0512767 | 11/1992 |
| EP | 0515484 | 12/1992 |
| EP | 0580305 | 1/1994 |
| EP | 0707077 | 4/1996 |
| WO | WO 95/13368 | 5/1995 |
| WO | WO 96/09116 | 3/1996 |
| WO | WO 96/18731 | 6/1996 |
| WO | WO 97/10331 | 3/1997 |
| WO | WO 97/29825 | 8/1997 |
| WO | WO 97/42975 | 11/1997 |
| WO | WO 99/29703 | 6/1999 |
| WO | WO 00/41547 | * 7/2000 |
| WO | WO 00/41647 | 7/2000 |
| WO | WO 02/48164 | 6/2002 |
| WO | WO 02/051382 | 7/2002 |

OTHER PUBLICATIONS

Gerald R. Reeck, et al., "Resolution of a Spectrum of Nucleoprotein Species in Sonicated Chromatin," *Proc. Nat. Acad. Sci. USA*, 69(8):2317-2321 (1972).

* cited by examiner

*Primary Examiner*—Ann Y. Lam

(57) ABSTRACT

Materials and method are disclose for delivering a desired substance to a target site, using a layered carrier in which the carrier and the substance together form at least three layers which associate by ionic interaction at the first pH, where at least one layer comprises a charge switch material which comprises an ionisable group and which has a positive charge at a first pH and a charge which is less positive, neutral or negative at a second pH, at least one layer comprises a polyionic polymer which is negatively charged at the first pH and at least one layer comprises the desired substance. Preferred carriers are based on the charge switch material poly Bis-Tris and the polyionic polymer polyacrylic acid.

44 Claims, 14 Drawing Sheets

Key: Nucleic Acid | Polycation PTV | Polyanion | Other Agent

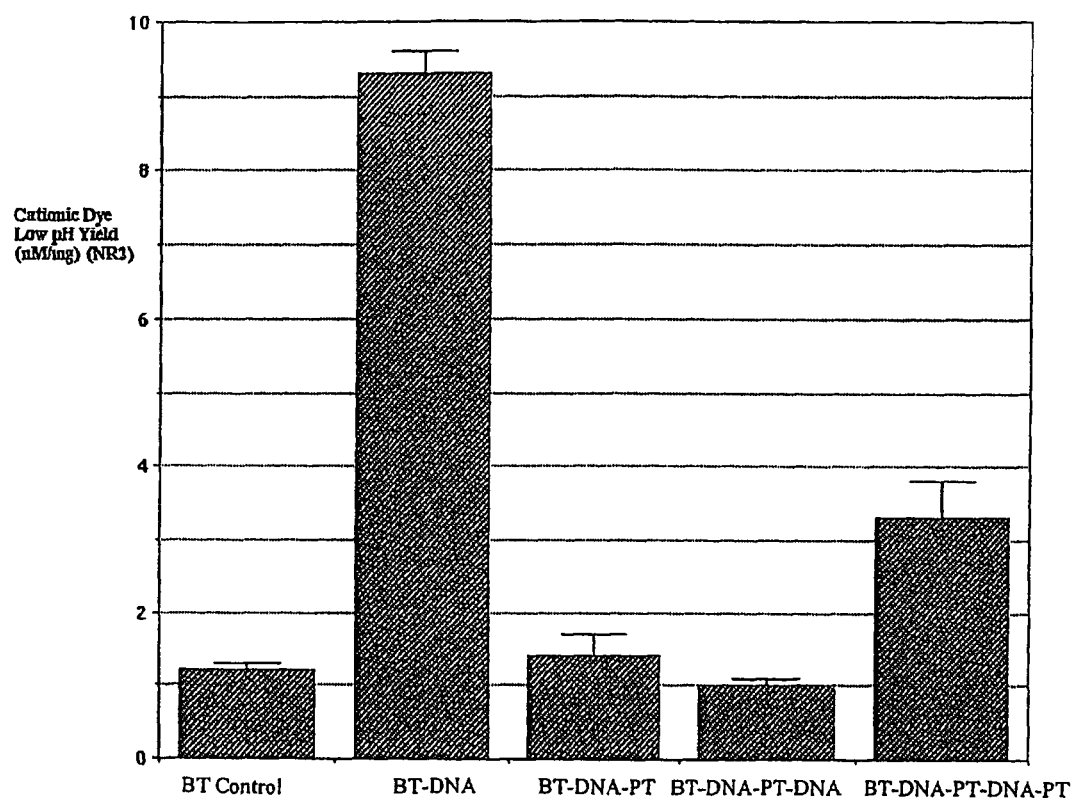

FIGURE 12

POLYION: EXPERIMENT GH200503
SIZE AND MOBILITY RESULTS FOR
MAGNETITE/POLYSTYRENE AGGREGATION
VERSUS POLSTYRENE-POLYCATION/MAGNETITE-POLYANION
AGGREGATION AND ELUTION

|  | Magnetite | Polyanion (Polyacrylic Acid) | Polystyrene Bead | Polycation (PolyTris) |
|---|---|---|---|---|
|  | MAG | +PA | PS | + PT |
| Size | 129nm (38) | 337 (25) | 186nm (2.5) | 370 (31) |
| Mobility | +38.1 mV | -21.8 | -40.6 mV | +33.3 |

AGGREGATE SIZES BEFORE AND AFTER ELUTION AT pH 8 & 11

| PolyIon | | INITIAL pH 4.0 | EB1 pH 8.0 | EB2 pH 11.0 | |
|---|---|---|---|---|---|
| PolyIon | Mag+PA + PS+PT | 412.6 (se 18) | 199.1 (se 90) | 120.3 (se 66) | Resuspend From Magnet |
|  |  |  | 238.7 (se 50) | 229.7 (se 27) | Supernatant with Magnet |
| Magnetite & Polystyrene Control | Mag + PS | 264 (9.8) (387)mag | 330.1 (se 16) | 272.7 (se 25) | Resuspend From Magnet |
|  |  |  | 43.5 (Clear) | 240.6 (se 20) | Supernatant with Magnet |

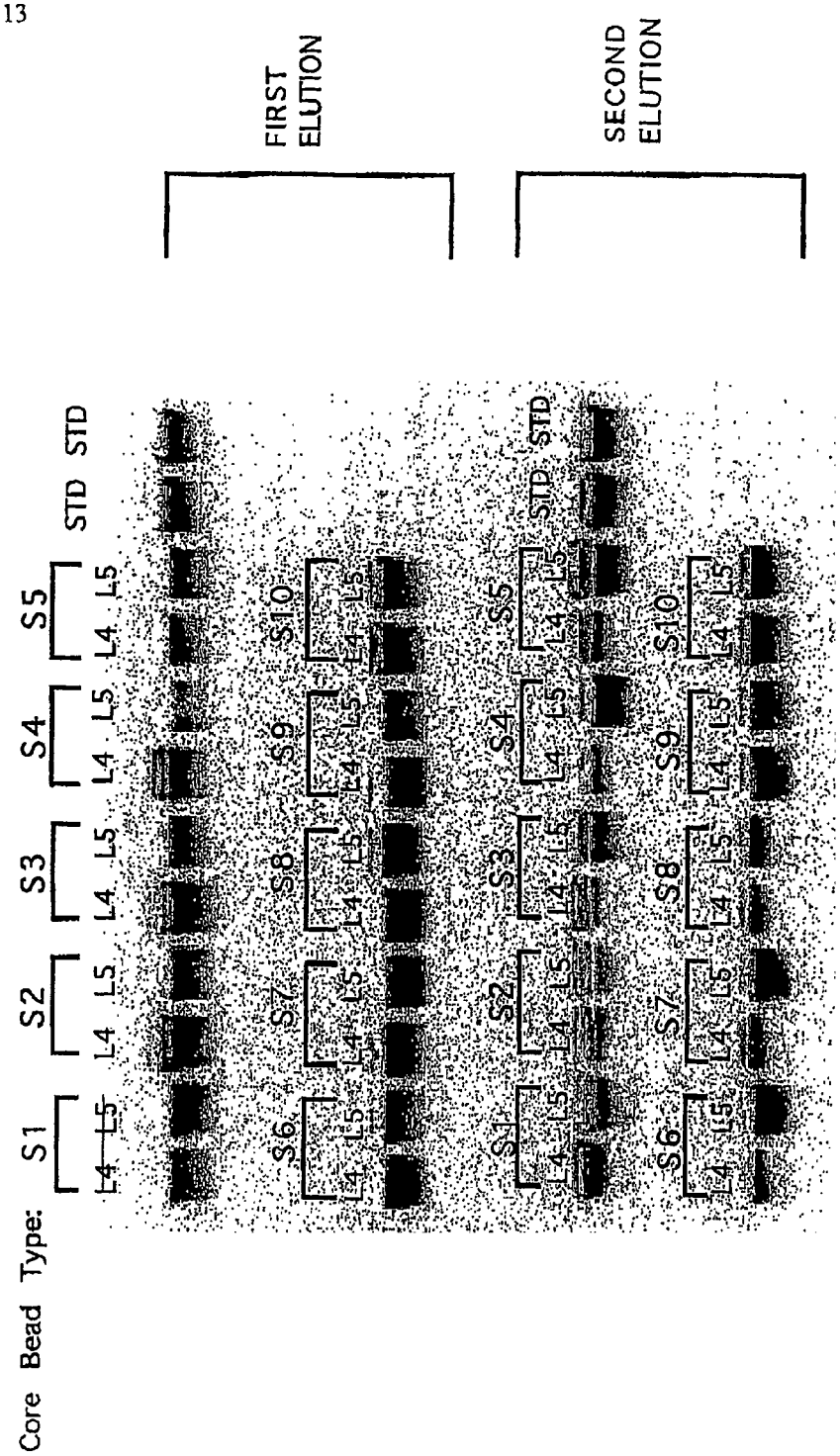

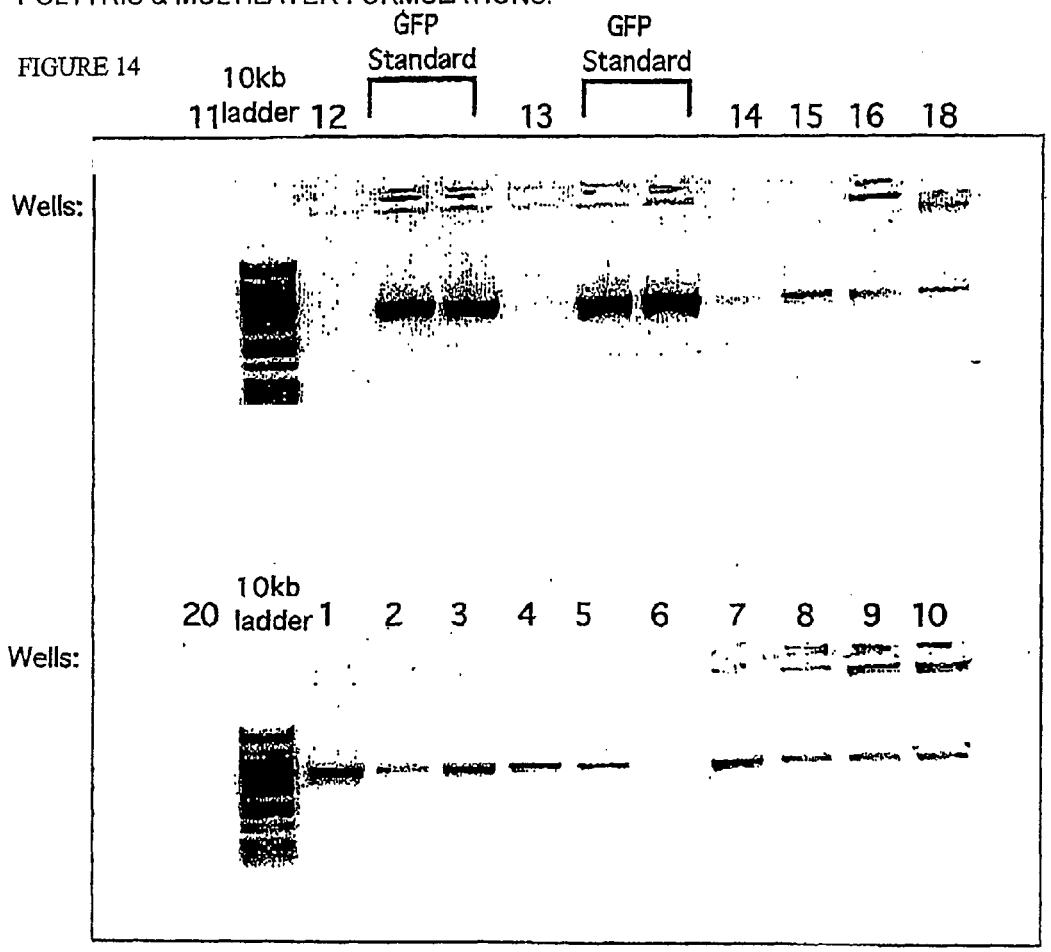

AGAROSE GEL OF GFP PLASMID DNA LOADING OF VARIOUS POLYTRIS & MULTILAYER FORMULATIONS.

FIGURE 14

Key to GFP Formulation Types:    [PL] = GFP Plasmid
1: $PT_{240}/[PL]$
2: Core $S6/PT_{240}[PL]$
3: $PT_{15}[PL]/PA_{15}$
4: $PT_{15}[PL]/PA_{15}/PT_{15}$
5: $PT_{240}[PL]/PA_{15}$
6: $PT_{240}[PL]/PA_{15}/PT240$
7: Core $S5/PT_{240}[PL]$
8: Core $S5/PT_{240}[PL]/PA_{240}$
9: Core $S5/PA_{240}/PT_{240}[PL]/PA_{15}/PT_{240}$
10: Core $S5/PA_{240}/PT_{240}[PL]/PT_{240}$
11: Core S5/PT/PA/PT[PL]/PA/PAM
12: Core S5/PT/PA/PT[PL]/PAM
13: $PT_{15}[PL]/PA_{240}$
14: $PT_{15}[PL]/PA_{240}/PT_{15}$
15: $PT_{15}[PL]$
16: Core $S6/PT/PA/PT[PL]/PT_{240}$
18: Core S6/PT/PA/PT[PL]/PAM
20: PolyTris 240

MATERIALS AND METHODS RELATING TO POLYIONS AND SUBSTANCE DELIVERY

FIELD OF THE INVENTION

The present invention relates materials and methods relating to polyions and substance delivery, and in particular to the use of materials comprising a charge switch material for substance delivery.

BACKGROUND OF THE INVENTION

There is a very large demand for DNA analysis for a range of purposes and this has lead to the requirement for quick, safe, high throughput methods for the isolation and purification of DNA and other nucleic acids. Samples for use for DNA identification or analysis can be taken from a wide range of sources such as biological material such as animal and plant cells, faeces, tissue etc. also samples can be taken from soil, foodstuffs, water etc.

Existing methods for the extraction of DNA include the use of phenol/chloroform, salting out, the use of chaotropic salts and silica resins, the use of affinity resins, ion exchange chromatography and the use of magnetic beads. Methods are described in U.S. Pat. Nos. 5,057,426 and 4,923,978, EP 0 512 767 A and EP 0 515 484 A and WO 95/13368, WO 97/10331 and WO 96/18731. These patents and patent applications disclose methods of adsorbing nucleic acids on to a solid support and then isolating the nucleic acids. The previously used methods use some type of solvent to isolate the nucleic acids and these solvents are often flammable, combustible or toxic.

EP 0 707 077 A describes a synthetic water soluble polymer to precipitate nucleic acids at acid pH and release at alkaline pH. The re-dissolving of the nucleic acids is performed at extremes of pH, temperature and/or high salt concentrations where the nucleic acids, especially RNA, can become denatured, degraded or require further purification or adjustments before storage and analysis.

WO 96/09116 discloses mixed mode resins for recovering a target compound, especially a protein, from aqueous solution at high or low ionic strength, using changes in pH. The resins have a hydrophobic character at the pH of binding of the target compound and a hydrophilic and/or electrostatic character at the pH of desorption of the target compound.

WO 99/29703 and WO 02/48164 disclose the use of charge switch materials for purifying nucleic acid, binding nucleic acid in a sample to a solid phase at a low pH (e.g. pH 6) and releasing the nucleic acid at a higher pH (e.g. pH 8). WO 99/29703 exemplifies the use of solid phases incorporating histidine or polyhistidine groups, and WO 02/48164 further exemplifies the use of charge switch materials such as biological buffer, for example Bis-Tris.

There is also considerable current interest in methods of carrying active molecules such as DNA, drugs and other therapeutic agents and delivering them to a target site, particularly a target site in vivo.

Existing methods for delivering DNA to a target site include the delivery of DNA using modified retroviruses or adenoviruses, direct injection of naked DNA into the organism, or use of liposomes.

Synthetic delivery systems such as liposomes are advantageous over viruses for a number of reasons, including a reduced risk of immunogenic reaction, and the possibility of increased carrying capacity. However, for cationic liposomes, the positive charge on the surface of the delivery envelope can result in non-specific tissue uptake and non-specific interaction with negatively charged serum molecules, blood cells and the extra-cellular matrix. These interactions also sometimes cause precipitation. Anionic liposomes, on the other hand, achieve low encapsulation as a result of the inability of the DNA to interact with the coating liposome.

An alternative method for delivering DNA involves forming a complex between DNA and a polycation (Cotton 1993, Current Opinion in Biotechnology V4 p 705). U.S. Pat. No. 5,908,777 describes a method of forming a lipidic vector for delivery of therapeutic molecules which entails forming a complex between the desired substance and a polycation such as polylysine, and then mixing the complex with an anionic lipid preparation.

U.S. Pat. No. 5,679,559 describes a method for introducing DNA into cells, which involves providing a core of lipoprotein. This is associated with hydrophobic side chains of a positively charged biocompatible polymer, which in turn is associated with a nucleic acid molecule. Because the polymer is carried on the surface of the particle, the amount of polymer that can be carried by the particle is limited.

U.S. Pat. No. 6,383,811 discloses a delivery system in which a complex of DNA and polycation is associated with a negatively charged polymer, to render the particle as a whole negatively charged and thus to make delivery easier. The negatively charged polymer can be a separate polymer added to preformed DNA/polycation complexes, or it can be covalently bound to the polycation to form a polyampholyte, which is then complexed with the DNA. However, there is no disclosure that the polycation or polyanion should have charge switch properties, such that release of the DNA is induced by a change in the pH environment. There is also no disclosure that the components of the particle should be arranged in a multi-layer structure.

SUMMARY OF THE INVENTION

Broadly, the present invention relates to novel methods of carrying and delivering desired substances to a target site and novel products for use therein. In some aspects, the present invention involves using charge switch materials to form polyions with other substances for use in delivering the substance or in the purification of nucleic acid.

In a first aspect, the present invention provides a method for delivering a desired substance to a cell, the method comprising:

contacting a carrier with the substance at a first pH, wherein the carrier comprises charge switch material having an ionisable group, and wherein the charge switch material has a positive charge at the first pH, such that the substance is bound to the charge switch material by ionic interaction;

delivering the carrier to a target site; and releasing the substance from the carrier at a second, higher pH at which the charge on the material is negative, neutral or less positive.

In a preferred embodiment, the carrier comprises at the first pH at least three layers which associate by ionic interaction, wherein one or more of the layers comprises the charge switch material.

The change in charge of the carrier material is referred to herein as "charge switching" and is accomplished by use of a "charge switch material".

The charge switch material comprises an ionisable group, which changes charge to according to the ambient conditions. The charge switch material is chosen so that the pKa of the ionisable group is appropriate to the conditions at which it is desired to bind nucleic acid to and release nucleic acid from the carrier. Generally, nucleic acid or other desired substance will be bound to the charge switch material at a pH below or roughly equal to the pKa, when the charge switch material is positively charged, and will be released at a higher pH (usually above the pKa), when the charge switch material is less positively charged, neutral, or negatively charged.

However, it is also possible that the charge switch binds a desired substance at a high first pH, and at which the charge switch material is negatively charged, and releases the desired substance at a second pH which is lower and at which the charge switch material is less negatively charged, neutral or positively charged.

The present invention is more particularly directed to the use of charge switch materials which allow releasing of the desired substance to occur under physiological conditions. The target site may be a target site in a cell, or it may be an extracellular target site, e.g., in or on the human or animal body or a plant. Accordingly, the invention has wide-spread applicability for the environmentally-dependent release of topical, enteral, oral and parenteral delivery of drugs and in gene therapies. In addition, the invention may be useful in cell containment and the pH dependent release of indicators, chemicals, organisms and bioactives in agrochemical, horticultural, fisheries, veterinary, biomedical industrial, nutraceutical, food and food-chain, cosmetics and defence industries.

Previous methods of delivering desired substances to cells include forming complexes between DNA and polycationic molecules, especially polylysine. However, the inventors have realized that the release of desired substance from such a complex is likely to be inefficient, as there is no mechanism for controlled release. By using charge switch materials, it is possible to obtain controlled release of desired substances in at a target site, by virtue of a change in the pH environment.

In second aspect, the present invention provides a carrier for delivering a desired substance to a target site. In one embodiment, the carrier comprises at least three layers which associate by ionic interaction, wherein at least one of these layers is a charge switch material and wherein the desired substance is bound to the carrier by ionic interaction. In another embodiment, the carrier comprises at least four layers which associate by ionic interaction, wherein at least one of these layers comprises a charge switch material, and wherein the desired substance is optionally bound to the carrier by ionic interaction.

The use of multiple layers in the carrier provides a means of increasing the carrying capacity of each carrier. This can be achieved in one of two ways. Firstly, desired substance can be incorporated into at least one layer of the carrier, as well as optionally being bound to the surface of the carrier. Thus in a preferred embodiment of the invention at least one of the layers, preferably one of the layers comprising a material having a plurality of negative charges, comprises a desired substance. This may be the same as or different from the desired substance bound to the outer surface of the carrier.

Moreover, the inventors have discovered that if consecutive layers of polyion having alternately positive and negative charges are built up, ending in a layer which comprises a polyion which is positively charged at a first pH, then the resultant product is capable of binding more of a negatively charged desired substance than a particle which has only a single layer comprising positively charged polyion. Therefore, in a further or additional embodiment of the invention, at least two layers of the carrier comprise a polyion. Preferably the layers are adjacent. More preferably desired substance is bound directly to the outermost of these layers.

The carrier may also be used for the isolation of desired substance, the improved carrying capacity of the carrier resulting in improved yield of desired substance.

A charge switch material is defined herein as a material which has an ionisable group and which is charged at a first pH and is uncharged, neutral or less charged at a second pH.

Generally the charge on the charge switch material will change because of a change in charge on a positively ionisable group from positive to less positive or neutral, as the pH is increases in a range spanning or close to the pKa of the positively ionisable group. This may also be combined with a change of charge on a negatively ionisable group from neutral or less negative to more negative. In an alternative embodiment (described below), however, the charge switch material comprises a material which is positively charged at both pH values (such as a metal oxide) and a negatively ionisable group, the charge of which becomes more negative as the pH is increased in a range spanning or close to its pKa.

The charge switch material may comprise an ionisable group having a pKa between about 3 and 9. For positively ionisable groups, the pKa is more preferably at least about 4.5, 5.0, 5.5, 6.0 or 6.5 and/or at most about 8.5, 8.0, 7.5 or 7.0. A particularly preferred pKa for a positively ionisable group is between about 5 and 8; even more preferred is a pKa between about 6.0 and 7.0, more preferably between about 6.5 and 7.0. The pKa for negatively ionisable groups is preferably between about 3 and 7, still more preferably between about 4 and 6, further preferably approximately at the pH at which it is desired to bind desired substance.

Materials having more than one pKa value (e.g. having different ionisable groups), or combinations of materials having different pKa values, may also be suitable for use as charge switch materials in accordance with the invention, provided that at a first (lower) pH the material(s) possess(es) a positive charge and that at a higher pH the charge is less positive, neutral or negative.

Generally, a charge switch will be achieved by changing the pH from a value below to a value above the pKa of the or an ionisable group. However, it will be appreciated that when the pH is the same as the pKa value of a particular ionisable group, 50% of the individual ionisable groups will be charged and 50% neutral. Therefore, charge switch effects can also be achieved by changing the pH in a range close to, but not spanning, the pKa of an ionisable group. For example, at the pKa of a negatively ionisable group, such as a carboxy group (pKa typically around 4), 50% of such groups will be in the ionised form (e.g. COO⁻) and 50% in the neutral form (e.g. COOH). As the pH increases, an increasing proportion of the groups will be in the negative form.

Preferably the binding step is carried out at a pH of below the pKa of the ionisable group, or (though this is not preferred) within about 1 pH unit above the pKa. Generally the releasing step is carried out at a pH above the pKa of the ionisable group, preferably at a pH between 1 and 3 pH units above the pKa.

Examples of suitable charge switch materials are described in the applications WO 99/29703 and WO 02/48164, the content of which are incorporated herein by reference. Examples of classes of charge switch materials include biological buffers, polyhydroxylated amines, detergents or surfactants, nucleic acid bases, heterocyclic nitrogen-containing compounds, monoamines, dyes and compounds having a negatively ionisable group, the pKa of which is between about 3.0 and 7.0 in combination with a metal oxide which is positively charged at said first pH, and optionally also at said second pH. They include histidine, polyhistidine, and biological buffers comprising positively ionisable groups which may be polymerized or joined to a polymeric backbone.

Broadly speaking, preferred chemical species for use as charge switch materials in accordance with the invention comprise a positively ionisable nitrogen atom, and at least one, but preferably more than one, electronegative group (such as a hydroxy, carboxy, carbonyl, phosphate or sulphonic acid group) or double bond (e.g. C=C double bond), which is sufficiently close to the nitrogen atom to lower its pKa. It has been found that such molecules tend to have suitable pKa values for the extraction of nucleic acid under mild conditions according to the present invention. Preferably at least one (but more preferably more than one) electronegative group is separated from the ionisable nitrogen by no more than two atoms (usually carbon atoms). Hydroxyl groups are particularly preferred electronegative groups (particularly when several hydroxyl groups are present, e.g. in polyhydroxyl amines, such as Tris ($C(CH_2OH)_3$—$NH_2$) or Bis-Tris (see below)), as they (1) lower the pKa of the nitrogen atom (e.g. amine group, e.g. from about 10 or 11) to a suitable value around neutral (i.e. pKa of about 7), (2) allow the species to remain soluble/hydrophilic above the pKa, when the nitrogen atom of the amine group loses its positive charge, (3) provide a site for covalent linkage to a solid substrate, e.g. a polycarboxylated polymer (such as polyacrylic acid), and (4) are uncharged at pH values suitable for the releasing step and at which procedures such as PCR are performed (typically pH 8.5); the presence of charged species can interfere with PCR especially. Especially preferred are chemical species having an ionisable nitrogen atom and at least 2, 3, 4, 5 or 6 hydroxyl groups. Further examples of polyhydroxylated amines are dialcohol amine reagents such as diethanol amine. Silane reagents based on these compounds can be used to attach [HO—$(CH_2)_n$]$_2$—N—$(CH_2)_m$— moieties, where n and m are selected from 1 to 10, to a solid phase e.g. using 3-bis(2-hydroxyethyl)aminopropyl-triethoxy silane.

Many standard, weakly basic, buffers are ideal chemical species to provide the ionisable groups of charge switch materials, as they have pKa values close to neutral (i.e. 7).

For use as a charge switch material, chemical species comprising ionisable groups can be immobilised onto solid supports (e.g. beads, particles, tubes, wells, probes, dipsticks, pipette tips, slides, fibers, membranes, papers, celluloses, agaroses; glass or plastics) in a monomeric or polymeric form via adsorption, ionic or covalent interactions, or by covalent attachment to a polymer backbone which is in turn immobilised onto the solid support. Alternatively, they can be incorporated into solid, insoluble forms (with or without attachment to a polymer backbone) which inherently exhibit charge switching, e.g. beads, particles, tubes, wells, probes, dipsticks, pipette tips, slides, fibres, membranes or plastics. In the present invention, the layers of polyionic polymer and the desired substance can be built up on such solid phases.

Solid phase materials, especially beads and particles, may be magnetisable, magnetic or paramagnetic. This can aid removal of the solid phase from a solution containing the released nucleic acid, prior to further processing or storage of the nucleic acid. The complexes of the present invention can be thus be built up around core particles such as beads. The examples provided herein use core particles which are magnetic beads and polystyrene particles.

Preferably the weakly basic buffers are biological buffers, i.e. buffers from the class of buffers commonly used in biological buffer solutions. Examples of biological buffers may be found in commercial chemical catalogues, such as the Sigma catalogue. Examples of suitable biological buffers for use in charge switch materials in accordance with the invention, and their pKa values, are as follows:

N-2-acetamido-2-aminoethanesulfonic acid ‡‡ (ACES), pKa 6.8;
N-2-acetamido-2-iminodiacetic acid ‡‡ (ADA), pKa 6.6;
amino methyl propanediol † (AMP), pKa 8.8;
3-1,1-dimethyl-2-hydroxyethylamino-2-hydroxy propanesulfonic acid † (AMPSO), pKa 9.0;
N,N-bis2-hydroxyethyl-2-aminoethanesulfonic acid †† (BES), pKa 7.1;
N,N-bis-2-hydroxyethylglycine † (BICINE), pKa 8.3;
bis-2-hydroxyethyliminotrishydroxymethylmethane ‡‡ (Bis-Tris), pKa 6.5;
1,3-bistrishydroxymethylmethylaminopropane ‡‡ (BIS-TRIS Propane), pKa 6.8;
4-cyclohexylamino-1-butane sulfonic acid (CABS), pKa 10.7;
3-cyclohexylamino-1-propane sulfonic acid (CAPS), pKa 10.4;
3-cyclohexylamino-2-hydroxy-1-propane sulfonic acid (CAPSO), pKa 9.6;
2-N-cyclohexylaminoethanesulfonic acid (CHES) pKa 9.6;
3-N,N-bis-2-hydroxyethylamino-2-hydroxypropane-sulfonic acid †† (DIPSO), pKa 7.6;
N-2-hydroxyethylpiperazine-N-3-propanesulfonic acid †† (EPPS or HEPPS), pKa 8.0;
N-2-hydroxyethylpiperazine-N-4-butanesultonic acid † (HEPBS), pKa 8.3;
N-2-hydroxyethylpiperazine-N-2-ethanesulfonic acid †† (HEPES), pKa 7.5;
N-2-hydroxyethylpiperazine-N-2-propanesulfonic acid †† (HEPPSO), pKa 7.8;
2-N-morpholinoethanesulfonic acid ‡ (MES), pKa 6.1;
4-N-morpholinobutanesulfonic acid †† (MOBS), pKa 7.6;
3-N-morpholinopropanesulfonic acid †† (MOPS), pKa 7.2;
3-N-morpholino-2-hydroxypropanesulfonic acid ‡‡ (MOPSO), pKa 6.9;
piperazine-N-N-bis-2-ethanesulfonic acid ‡‡ (PIPES), pKa 6.8;
piperazine-N-N-bis-2-hydroxypropanesulfonic acid †† (POPSO), pKa 7.8;
N-trishydroxymethyl-methyl-4-aminobutanesulfonic acid † (TABS), pKA 8.9;
N-trishydroxymethyl-methyl-3-aminopropanesulfonic acid †† (TAPS), pKa 8.4;
3-N-trishydroxymethyl-methylamino-2-hydroxypropane-sulfonic acid †† (TAPSO), pKa 7.4;
N-trishydroxymethyl-methyl-2-aminoethanesulfonic acid †† (TES), pKa 7.4;
N-trishydroxymethylrnethylglycine † (TRICINE), pKa 8.1; and
trishydroxymethylaminomethane † (TRIS), pKa 8.1;
histidine*, pKa 6.0, and polyhistidine ‡‡;
imidazole*, pKa 6.9, and derivatives* thereof (i.e. imidazoles), especially derivatives containing hydroxyl groups**;

triethanolamine dimers, oligomers and polymers; and di/tri/oligo amino acids, for example Gly-Gly, pKa 8.2; and Ser-Ser, Gly-Gly-Gly, and Ser-Gly, the latter three having pKa values in the range 7-9.

In a preferred embodiment, the buffers marked above with an asterisk (*) are not considered to be biological buffers for the purposes of the invention (whether or not they are designated as such in any chemical catalogue). In a more preferred embodiment, those marked with two asterisks (**) are also not considered to be biological buffers. Preferred biological buffers are marked with a dagger (†), more preferred buffers are marked with two daggers (††), still more preferred buffers are marked with a double dagger (‡) and most preferred buffers are marked with two double daggers (‡‡).

These and other chemical species comprising ionisable groups may be coated as monomers onto a solid phase support using covalent, ionic or adsorption interactions. Additionally or alternatively, they may be coated onto such solid phase supports in polymeric form (preferably following condensation polymerisation), for example by adsorption onto a negatively charged surface (e.g. a surface having exposed COOH or $SO_3$ groups), or by covalent attachment. Additionally or alternatively, the chemical species containing ionisable groups may be attached to a polymer (see below) which is then attached to a solid support, e.g. by adsorption or covalent attachment.

Preferably the chemical species or polymer backbones are covalently coupled to the solid support via a hydroxyl group or other group so that the ionisable group having the desired pKa value (usually, but not limited to, a nitrogen atom) remains capable of binding and releasing nucleic acid.

Biological buffers and other chemical species comprising positively ionisable groups may be used in conjunction with a chemical species containing a negatively ionisable group which has a suitable pKa, preferably in the ranges described above. For example, a biological buffer (having one or more positively ionisable nitrogen atoms) may be attached to a polymer or other solid phase material which has exposed carboxy groups even after attachment of the biological buffer. Such a material may bind nucleic acids at a low pH when few of the carboxy groups are negatively charged (i.e. few are in the $COO^-$ form, most being in the COOH form) and most of the ionisable nitrogen atoms are positively charged. At higher pH the negative charge is stronger (i.e. a greater proportion of carboxy groups are in the $COO^-$ form) and/or the positive charge is weaker, and the nucleic acid is repelled from the solid phase.

Chemical species containing ionisable groups (such as the biological buffers listed above) can be attached to a polymer backbone using known chemistries. For example a chemical species containing a hydroxyl group can be attached using carbodiimide chemistry to a carboxylated polymer backbones. Other chemistries include can be employed by someone skilled in the art using other polymer backbones (e.g. based on polyethylene glycol (PEG) or carbohydrate) using a range of standard coupling chemistries (see e.g. Immobilised Affinity Ligand Techniques, Greg T. Hermanson, A. Krishna Mallia and Paul K. Smith, Academic Press, Inc., San Diego, Calif., 1992, ISBN 0123423309, which is incorporated herein by reference in its entirety.)

Alternatively, the chemical species containing ionisable groups can be polymerised without a backbone polymer, using cross-linking agents, for example reagents that couple via a hydroxy group (e.g. carbonyldiimidazole, butanediol diglycidyl ether, dialdehydes, diisothiocyanates). Polymers may also be formed by simple condensation chemistries to generate polymeric amino acids with the appropriate pKa e.g. Gly-Gly.

Preferably such immobilisation, attachment and/or polymerisation of the chemical species containing the ionisable group does not affect the pKa of the ionisable group, or leaves it in the desired ranges given above. For example it is generally preferred not to couple or polymerise the chemical species via a positively ionisable nitrogen atom (in contrast for example to WO 97/2982). In the practice of the invention, it is especially preferred to immobilise, attach and/or polymerise the chemical species via an hydroxyl group.

A preferred buffer for use as a charge switch material according to the invention is Bis-Tris, which may be polymerized by attachment to a polymer backbone such as polyacrylic acid. In this application, a Bis-Tris polymer formed by attachment of Bis-Tris monomers to a polyacrylic acid backbone or similar is termed "polyBis-Tris".

PolyBis-Tris can be produced by reacting Bis-Tris monomer with polyacrylic acid using 1-ethyl-3-dimethylaminopropyl carbodiimide (EDC). The polymer can then be easily separated from the reactants using dialysis against a suitable reagent or water. Preferably, the polyacrylic acid has molecular weight of between about 500 and 5 million or more. More preferably it has a molecular weight of between 100,000 and 500,000.

The nature of the resultant Bis-Tris/polyacrylic acid molecule will depend on the ratio of the coupled components, since the polymer will have different properties depending on the proportion of the acrylic acid groups that are modified with Bis-Tris, for example it is desirable for some carboxy groups to remain unmodified, as the presence of these will not prevent the Bis-Tris from binding nucleic acid at low pH (especially if the Bis-Tris is in excess), but their negative charge at higher pHs will assist with release of the nucleic acid. For use in the present invention, the molar ratio of Bis-Tris:carboxy groups (before attachment) is preferably between 5:1 and 1:5, more preferably between 3:1 and 1:3, still more preferably between 2:1 and 1:2, further preferably between 1.5:1 and 1:1.5, and most preferably about 1:1.

An alternative embodiment of the present invention uses a material which is positively charged across a wide pH range, such as 0-12 or 0-14 (e.g. an electropositive substance such as a metal oxide, metal, strong or weak base, which lacks a pKa value, or for which the pKa value is at an extreme of high pH). Such a positively charged material is combined with negatively ionisable material having a pKa intermediate between the pH values at which it is desired to bind and release nucleic acid, or slightly below the pH at which it is desired to bind nucleic acid. This combination of materials allows nucleic acid to be bound at certain pH values, around and below the pKa of the negatively ionisable material, when there are fewer negatively charged groups, but allows the nucleic acid to be released when the pH is increased and a greater number of the ionisable groups are negatively charged. For example, the combination of iron II, III oxide and polycarboxylates binds nucleic acid at pH 4, when a relative scarcity of negative charges allowing the positively charged iron oxides to bind the nucleic acid. When the pH is increased to around 8, a large proportion of the carboxy groups become negatively charged and, despite the remaining presence of positive charges on the iron oxides, the reduction in overall positive charge allows the nucleic acid to be released.

Further examples of charge switching molecules for nucleic acid purification are based on detergents or surfactants that have a hydrophobic portion and a hydrophilic portion which comprises a positively ionisable group with a suitable pKa, e.g. decyl methyl imidazole or dodecyl-Bis-Tris. These detergents or surfactants can be adsorbed onto surfaces e.g. plastic via their hydrophobic portions and the hydrophilic (ionisable) portions can be used to capture nucleic acid.

Another group of materials with suitable pKa values are nucleic acid bases, e.g. cytidine (pKa 4.2). These can be immobilised via hydroxy groups to a polymer or solid phase carboxy group using carbodiimides.

A still further group of materials having members with suitable pKa values are heterocyclic nitrogen-containing compounds. Such compounds may be aromatic or aliphatic and may be monomers, oligomers or polymers, such as morpholine-, pyrrole-, pyrrolidine-, pyridine-, pyridinol-, pyridone-, pyrroline-, pyrazole-, pyridazine-, pyrazine-, piperidone-, piperidine-, or piperazine-containing compounds, e.g. polyvinylpyridine. Such compounds may be substituted with electronegative groups to bring the pKa value(s) of the ionisable nitrogen atom(s) into an acceptable range, e.g. as defined above. However, in some compounds this may not be necessary, the pKa already being in such a range.

A still further group of solid phases for binding nucleic acid have surface amine groups, and in particular amine groups which are not polyamines. These monoamine groups can be represented by the formula —$NR_1R_2$, where $R_1$ and $R_2$ are hydrogen or substituted or unsubstituted alkyl. Although these materials typically have pKa values which at higher than those of materials used in preferred embodiments of the invention, they can be employed in the extracting of nucleic acid, optionally employing them with negatively charged species as described herein to modify the overall pKa of the solid phase.

A further group are materials that provide ionisable groups capable of acting as charge switch materials and binding nucleic acid are dyes, and in particular biological dyes having pKas between 5 and 8. These materials can be immobilised or coated on solid phases.

The materials and methods of the invention may be useful for delivering a bioactive substance to a target site which is on or in the animal or human body or in a plant. The pH of blood is normally around pH 7.4, while the pH of the cytoplasm is normally between pH 7.1 and 7.2. Similarly, the invention may be used for pH dependent release of a substance in soil or water, which will also have a pH which is not far from neutral. The pKa of the charge switch material can be selected to optimise release in these conditions.

The desired substance may be bound directly or indirectly to the charge switch material. In some embodiment, it is bound directly to the charge switch material so that it is released from the carrier as an ionic species. In these circumstances, it is preferred that the substance for delivery is negatively charged. However, it is also possible that the desired substance may be bound to the charge switch material via an intermediate layer or layers. For example, a positively charged substance may be bound to the charge switch material at the first pH via a layer of negatively charged counterion. At the second pH, the substance will be released from the carrier in association with its counterion.

In some embodiments of the invention disclosed in the examples, the charge switch material is used in conjunction with a polyionic polymer such as polyacrylic acid. As the charge switch material is generally positively charged at the first pH and the polyionic polymer is negatively charged, this makes it possible to transport desired substances which are positively charged, negatively charged or zwitterionic. Moreover, as shown in the examples these species have the surprising advantage or providing substantially increased loading of the desired substance compared to either component alone.

In addition, after binding the desired substance it is possible to bind a further layer which comprises a material which is not charge-switch, or which has a very high pKa. This is intended to stabilise the carrier during a transport step, and/or to delay the release kinetics. Again, it is likely that the desired substance will then be released with this counterion.

The desired substance for delivery may be selected from bioactive agents, including nucleic acids, pharmaceutically active compounds, proteins, carbohydrates, growth factors, hormones, enzymes, vaccines, cells, cell components and viruses. In addition, it may be a chemical selected from fertilisers, pesticides, insecticides, herbicides, fungicides, vitamins or feed supplements, imaging agents (including radiodiagnostic agents), dyes and chelating agents. Preferably, the desired substance is a bioactive agent, and most preferably it is a nucleic acid. In particular, in one aspect, the present invention in particular provides a method of transfecting cells with nucleic acid using the carriers disclose herein.

Preferably, the charge switch material is a particle or molecule comprising a plurality of groups which are positively charged at the first pH. More preferably, at the first pH the charge switch molecule is a polycation, that is a polymer which may be linear or branched, and comprises a plurality of monomer units having one or more groups which are cationic at the first pH. Examples of suitable polycations include polyhistidine and polyBis-Tris. Other suitable polycations are described in WO02/48164, the contents of which is incorporated herein by reference.

In a preferred embodiment, the carrier comprises at the first pH multiple layers, which associate by ionic interaction.

The layers may comprise zwitterionic materials, such that each layer has a positively charged face and a negatively charged face, allowing them to assemble into multiplayer structures by ionic interaction.

Alternatively, each layer may comprise a material which has a plurality of ionisable groups of the same charge. The material may be a particle, a molecule (e.g., a low molecule weight molecule or a polyion) or a derivatised solid surface or core (especially for the base layer). In this case, it is possible to build up multiple layers which are alternately positively and negatively charged.

Methods of building up multiple layers of alternately positively and negatively charged material are described in Decher et al., Thin Solid Films 244 (1994) 722, Lvov et al., Colloids and Surfaces A 146 (1999) 337, and Ariga et al., J. Am Chem. Soc. 119 (1997) 2224, the contents of which are incorporated herein by reference. Decher et al and Lvov et al. describe methods of building up alternate layers of polycation and polyanion while Ariga et al. describe a method of building layers of polycation with layers of small dye molecules having a plurality of negative charged groups. The underlying principle for assembly in each case appears that in each layer, a surplus of charge is absorbed relate to the amount of charge needed to neutralise the charge on the forgoing layer. This surplus charge allows the subsequent, oppositely charged layer to be bound.

A polyion is a polymer comprising a plurality of monomer units which have an ionisable group. The polymer may comprise only a single type of monomer units or it may comprise more than one type (i.e., it may be a copolymer).

A polycation comprises a plurality of monomers having a positively ionisable group. It may also comprise negatively ionisable groups, but at the first pH it will be positively charged overall. Similarly, a polyanion comprises a plurality of monomers having negatively ionisable groups and is negatively charged at the first pH, though it may also comprise some positively ionisable groups.

It is possible that the polycation or polyanion may form part of a larger molecule, possibly being covalently linked to a polyion of the opposite charge. A molecule of this sort, which comprises a section which is a polycation and a section which is a polyanion, is known as a polyampholyte. When assembling layers, these polyions will act as zwitterionic molecules, to provide a layer having a negative face and a positive face.

The polyion may be linear, cyclic or branching. Preferably it is linear.

Examples of polyanions for use in accordance with the present invention include.

Polyanions:
Type—Functional Anion Group—Merck Index#
Acetylated polyglucoronate COOH
Acidic polysaccharides COOH
Alginic Acid/Alginates COOH M1835
Ascophyllan $SO_3H$
Carrageenan Sulphated Galactoses M1872
Carbomer (Polyvinylcarboxyl) COOH M1836
Carboxylated Polyethylene Oxide COOH
CarboxymethylCellulose (CMC) COOH M1835
CarboxymethylDextran COOH
Citraconic Acid COOH M2323
Citric Acid COOH M2328
Chondroitin Sulfate $SO_4$ M2217
Dexoxyribonucleic acid $PO_4$
Ribonucleic acids $PO_4$ M8204
Dextran sulfate $SO_3H$—AntiCoagM2929
EDTA (ethylenedinitrilo tetracetic acid COOH M3483
Fucoidan $SO_3H$
Fumaric acid COOH 4200
PolyFumaric acid COOH 4200
Heparin (sulfate) $SO_4$ M4571
Hyaluronic acids/Hyaluronate COOH
Oxidized Cellulose COOH
Multibasic acids COOH
Nucleic acids $PO_4$
Pectins/Pectate COOH
Pentosan polyphosphate $PO_4$
Pentosan polysulfate [$SO_4$] $SO_3H$ M7090
Phosphated Polyethylene oxide $PO_4$
Polyaspartic acid COOH M862
Polyacrylic acid COOH
Polycarboxyaspartic acid COOH M1833
Polyamino acids COOH/$NH_2$
Polycarboxylic acid COOH
Polycarboxyglutamic acid COOH M1834
Polycinnamic acid COOH M2300
Polycysteine SH
Polyestradiol phosphate $PO_4$ M7542
Polygalacturonic acid COOH M4242
Polyguluronic acid COOH
Polyglucuronic acid COOH M4360
Polyglutamic acid COOH M4363
Polyglutathione COOH/SH M4369
Polyglyerol phosphate, Teichoic acid $PO_4$ M9061
PolyGlycolic Acid (PGA) COOH
Polyhydroxycarboxylic acids COOH
Polyiduronic acid COOH M4571
PolyLactic Acid (PLA) COOH
Polymaleic acid COOH M5585
Polymannuronic Acid/Polymannuronate COOH
Polynulceotides $PO_4$ M6647
Polypeptides COOH/$NH_2$/SH
Polyphosphate $PO_4$
Polyribitol phospahte $PO_4$ M9061
Polyvinyl acetate (PVA) [COO] COOH
Sulfated Polyethylene oxide $SO_4$
Tribasic carboxyacids COOH
Dibasic CarboxyAcids COOH
Tartaric Acid COOH M9039
Xylan Hydrogen Sulfate $SO_3H$ M7090

A preferred polyanion for use in the present invention is polyacrylic acid, for example having a molecular weight between 10 k and 500 k, more preferably between 100 k and 300 k.

In one embodiment of the invention, the carrier comprises at least three layers which associate by ionic interaction, wherein at least one of the layers comprises a charge switch material and wherein a desired substance is bound to the carrier by ionic interaction. In another embodiment, the carrier comprises at least four layers which associate by ionic interaction, wherein at least one of the layers comprises a charge switch material and wherein a desired substance is optionally bound to the carrier by ionic interaction. The carrier may comprise at least 5, optionally at least 6, 7, 8, 9 or more layers.

The use of multiple layers in the carrier provides a means of increasing the amount of desired material that can be carried thereby. The present inventors have identified two ways in which this can be achieved.

Firstly, an increase in the amount of substance to be carried can be achieved by incorporating a desired substance into one or more layers. Accordingly, in one embodiment of the invention, at least one layer of the carrier comprises desired substance.

This desired substance may be positively charged, negatively charged, zwitterionic or neutral. If the layers of the carrier are alternately positively and negatively charged, then preferably, the desired substance has the same charge as the layer into which it is integrated, in which case it will bind to the underlying layer by ionic attraction and will be released as an ionic species. The desired substance need not comprise a plurality of charged groups, provided that the layer as a whole comprises more charge that is required to neutralise the charge on the preceding layer. Alternatively, and in a less preferred embodiment, the further desired substance may be neutrally charged, and may be incorporated into the layer by entrapment.

The desired substance incorporated into or forming one or more layers may be same as or different from desired substance bound to the surface of the carrier. Similarly, if desired substance is incorporated into or forms more than one layer, then the substance in each of these layers may be the same or different. The desired substance may be selected from bioactive agents, including nucleic acids, pharmaceutically active compounds, proteins, carbohydrates, growth factors, hormones, enzymes, vaccines, cells, cell components and viruses. In addition, it may be a chemical selected from fertilisers, pesticides, insecticides, herbicides, fungicides, vitamins or feed supplements, imaging agents (including radiodiagnostic agents), dyes, chelating agents, cosmetics, paints, adhesives, detergents, lipids, food supplements or neutraceuticals. Preferably, the desired substance is a bioactive agent, and most preferably it is a nucleic acid. In this context, 'nucleic acid' single or double stranded nucleic acid and may include genomic DNA, cDNA or RNA. The nucleic acid may be wholly or partially synthetic. Nucleic acid may be used in accordance with the present invention by itself or linked to other sequences, e.g. a carrier or expression vehicle such as a plasmid.

The present invention may employ an enzyme as the desired substance. Enzymes are catalytic polypeptides and the skilled person can readily find examples of enzymes for use in accordance with the present invention. By way of a brief illustration, representative examples of the six classes are: Lactate dehydrogenase (LDH) (IUB 1.1.1.27) an oxidoreductase that catalyses L-lactate to pyruvate with the reduction of NAD+ to NADH; hexokinase (2.7.1.1), pyruvate kinase (2.7.1.40) and DNA-dependent RNA polymerase (2.7.7.6) are three transferases; hydrolases such as ribonuclease A (3.1.4.22), lysozyme (3.2.1.17) and trypsin (3.4.21.4); enolase (4.2.1.11) a lyase; triose phosphate isomerase (5.3.1.1) an isomerase, and glutamine synthetase (6.3.1.2) a ligase (synthetase).

Preferably, the carrier is comprises layers which alternatively comprise a material which is positively charged at the first pH at a material which is negatively charged at the first pH (i.e., layers of alternate charge). Preferably, desired substance is incorporated into one or more negatively charged layers. More preferably, the desired substance in one or more negatively charged layers comprises a plurality of negatively charged groups on the same molecule or particle. In a still more preferred embodiment, the desired substance in one or more negatively charged layers is a polyion, still more preferable a linear polyion and more preferably still a nucleic acid.

It will be clear that where the desired substance is itself a particle or molecule comprising a plurality of negatively charged groups then there will be no need to include any other such material in the negatively charged layer, i.e., the layer can be formed largely or entirely from the desired substance.

If desired substance is incorporated into or forms one or more layers of the carrier, then it is clearly desirable to release this target material at the target site. In order that this might be achieved, at least one layer underlying the layer comprising the target material, and/or the layer comprising the target material, should comprise a charge switch material. It preferred that the substance is released without being associated with any other components of the carrier, and so it is preferred that both the layer immediately underlying the layer comprising charge switch material, and the layer immediately overlying it (if there is one) comprise charge switch material. It is also preferred that the further desired substance is neutral or has the same charge as the material in the layer in to which it is incorporated, so that it does not remain associated with any component of this layer.

The inventors have additionally realised that if consecutive layers of polyion having alternately positive and negative charges are built up, ending in a layer which comprises a polyion which is positively charged at a first pH, then the resultant product is capable of binding more of a negatively charged desired substance than a particle which has only a single layer comprising positively charged polyion.

Without wishing to be bound by theory, it is believed that the reason for this is that when the first layer of polyion is laid down, it does not lie completely flat against the substrate, but will have portions which lie against the substrate and portions which extend away from the substrate. These portions which extend away from the substrate do not necessarily contribute to neutralization of the charge on the underlying layer, but represent surplus charge which is available for binding the next layer. The orientation of these portions away from the surface, combined with the fact that they carry multiple charged groups, results in there being a high density of charge per unit of surface area. It is therefore possible to bind a greater quantity of oppositely charged polyion in the next layer, which in turn results in an increased charge density per unit area. As a result, an increased amount of desired substance can be bound to the surface of the carrier.

Thus, in a preferred embodiment of the invention, at least two layers comprise a polyion. Preferably the layers comprising polyion are adjacent. It is also preferred that desired substance is bound directly to the outermost of these layers, in order to obtain the maximum benefit in the carrying capacity.

This increase in the carrying capacity is useful both for the delivery of substance to a target site (allowing more of the substance to be carried on each bead) and for isolation of a substance from a sample, allowing a greater yield to be produced from an equivalent number of beads.

It will be apparent that in a multi-layer product, both of the improvements in carrying capacity described above can be obtained simultaneously. The greatest advantage will be obtained if the carrier comprises of layers which alternately comprise a polyanionic desired substance, such as nucleic acid, and a polycationic charge switch material.

The carrier according to the invention may be a carrier particle, such as a bead. The particle may comprise a core which is a solid material. Alternatively, the carrier may be a pipette tip, a container or a filter coated with the materials according to the invention. The solid core or surface may be derivatized with a charged group (e.g., a carboxy group) to allow further layers to be built up by ionic association, and it may itself be a layer according to the invention.

A bead can also be formed with a core of particulate material which may be a charge switch polycation, or a polyanion. For example, certain polyBis-Tris polymers have a natural tendency to take a particulate form, while DNA can be precipitated with couterions to form a "core".

In a further aspect, the present invention provides for use of a carrier as described above in method of treatment of the human or animal body by therapy, which comprises providing a carrier according to the invention to a cell, wherein the carrier comprises desired substance and the desired substance is released at an intracellular pH.

The invention also provides for use of a carrier according to the invention in a method of delivering a desired substance to a target site. The target site may be intracellular. The method may be carried out in vitro or in vivo.

Further, the present invention provides a method of isolating nucleic acid from a sample, the method comprising:
at a first pH, bringing the sample into contact with a carrier according to the invention, such that the nucleic acid is bound to the carrier; and
releasing the nucleic acid at a second, higher pH at which the charge on the material is negative, neutral or less positive.

Embodiments of the present invention, in its various aspects, will now be described in more detail by way of example only.

BRIEF DESCRIPTION OF THE DRAWINGS

FIG. 11 shows the yield of cationic dye by elution at low pH from beads having a various number of layers of DNA and polyBis-Tris (PT).

FIG. 12 shows size and mobility results for magnetite/polysytrene aggregation results discussed in Example 28.

FIG. 13 shows an agarose gel of genomic calf-thymus DNA release from multilayer preparations on different Core Beads [S1 though S10] with 4 layers [L4]: Core-PAM-PA-PT-DNA and 5 layers [L5]: Core-PAM-PA-PT-DNA-PT, see also Example 31.

FIG. 14 shows an agarose gel of GFP plasmid DNA loading of various PolyTris and multilayer formulations, see also Example 32.

EXAMPLES

Materials

Figure 1:
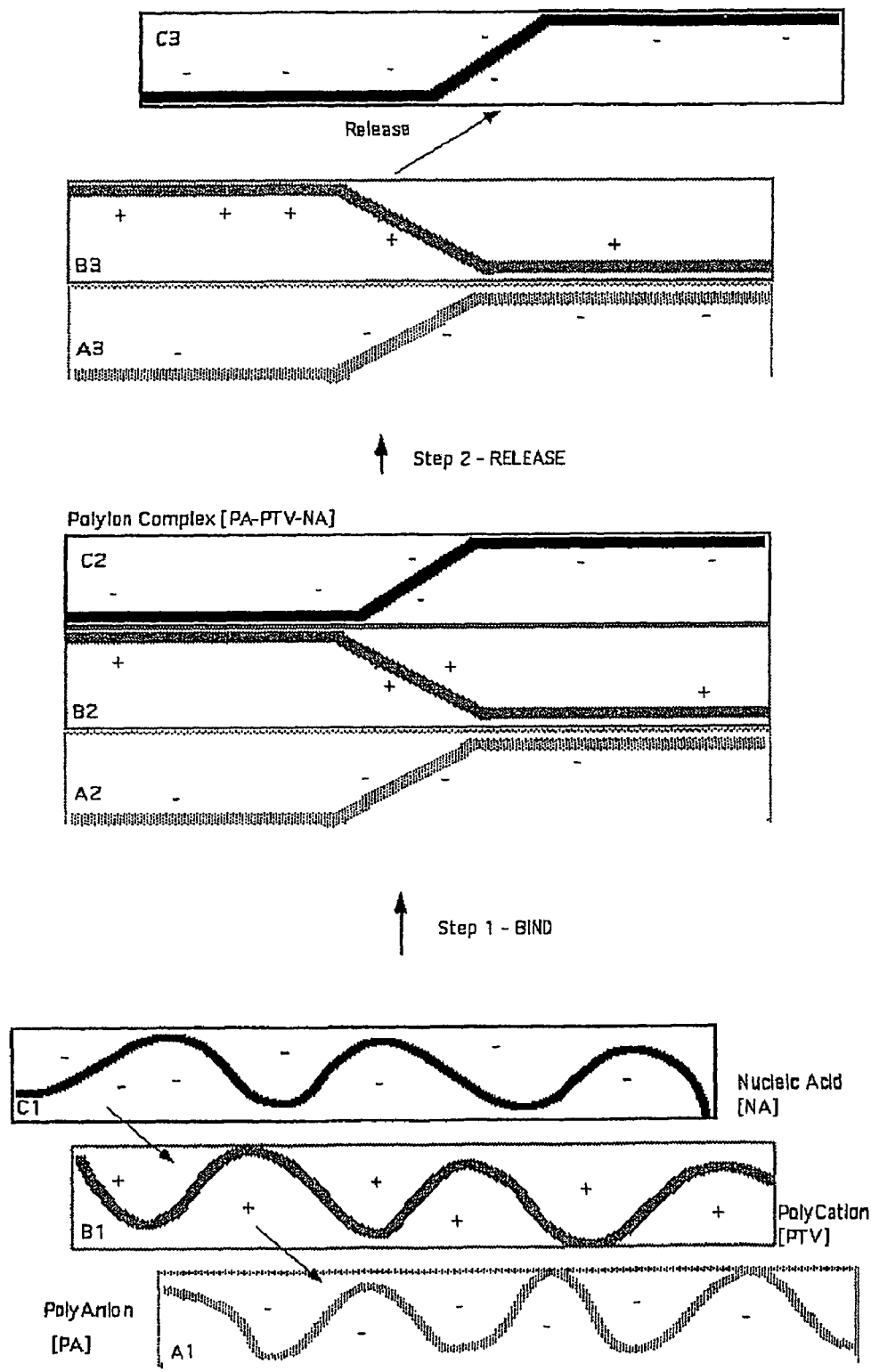
FIG. 1 shows a schematic representation of the formation of a multi-layer polyanion/polycation structure comprising DNA, and the release of DNA from this structure.
Figure 2:
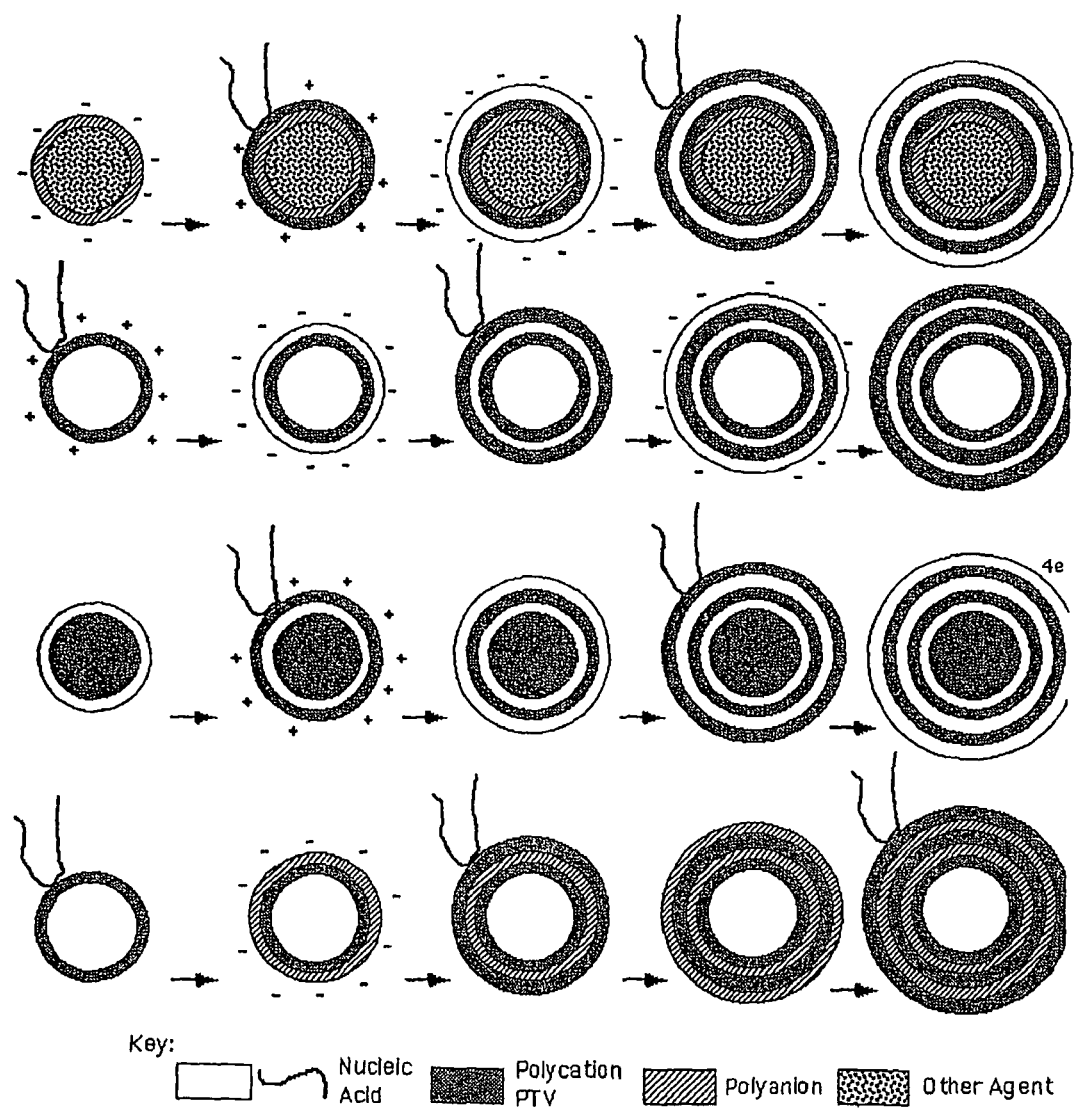
FIG. 2 and FIG. 3 show a schematic representation of various multi-layer carriers according to the invention.
Figure 3:
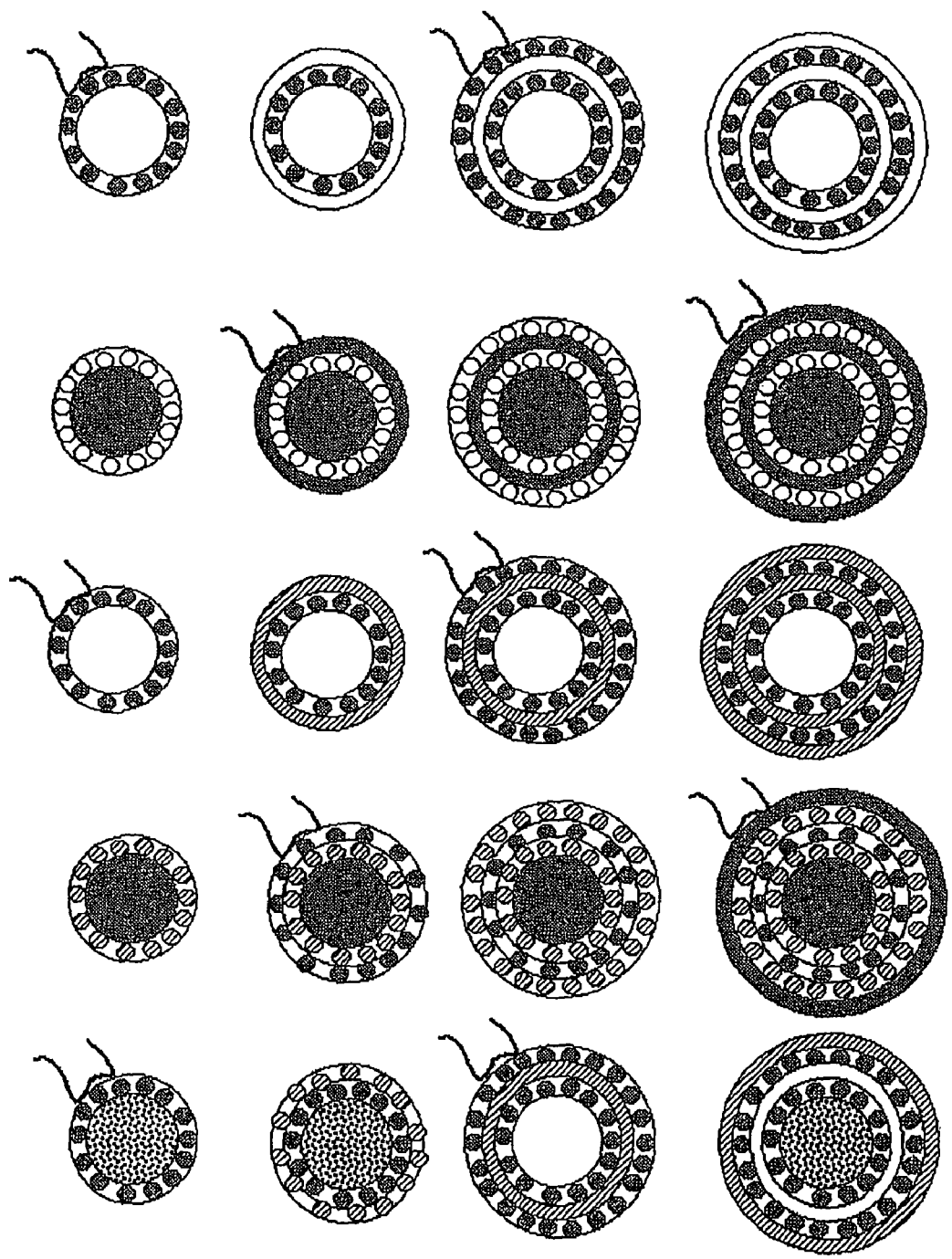

Precipitation Buffer [PB] consists of 1M Potassium Acetate, 0.66M Potassium Chloride. PB/100 comprises a 1:99 dilution of PB providing 10 mM Potassium Acetate and 7 mM Potassium Chloride Elution Buffer [EB]—comprises 10 mM Trizma Base and 1 mM Trizma HCl Example 1

PolyBis-Tris Polymer Formation

Bis-Tis monomer was converted into a polymer by mixing together 160 mg of polyacrylic acid with a molecular weight of 240,000, 1.6 g of Bis-Tris and 1.6 g of EDC in 50 mM imidazole pH6.0. Following an overnight incubation, the mixture was dialyzed in water.

Example 2

PolyBis-Tris Polymer Formation

In an alternative method, polyBis-Tris polymer was prepared using polyacrylic acid (PAA) with a molecular weight of either 15,000 or 450,000. 100 mg of PAA polymer was mixed with 30 ml of 0.1M Imidazole (HCl) pH 6.0 and 1 gm of BisTris. The buffer was adjusted to between pH 6.0 and 7.0 using NaOH, and 1.0 gm of (EDC) was added as solid. The tube was vigorously inverted by hand for one minute, and mixed by inversion 14 hours.

The resulting mixture was dialyzed in water.

Example 3

Bis-Tris Solid Phase Magnetic Beads 112 mg of carboxylated 1 µm magnetic particles were reacted in a one step procedure with 110 mg of Bis-Tris and 110 mg of the carbodiimide, EDC, in 0.1M imidazole HCl pH6.0. Following an overnight incubation, the magnetic particles were washed. The particles can be used as described below.

Example 4

Bis-Tris Solid Phase Polystyrene Beads 1 gram of carboxylated 60 µm polystyrene particles were reacted in a one step procedure with 500 mg of Bis-Tris and 500 mg of the carbodiimide, EDC, in 50 mM imidazole buffer pH6.0. Following an overnight incubation, the particles were washed. The particles can be used in a method as described below.

Example 5

Immobilised Poly Bis-Tris on Pipette Tips

A solution of polyBis-Tris at 1 mg/ml, prepared as in Example 1 or 2, in 0.1M sodium bicarbonate pH8 was incubated at 60° C. for 8 hours with twenty 200 µl polyproplylene pipette tips. These tips can then be used in a method as described below.

Example 6

Formation of Beads with Multiple Layers of Polyacrylic Acid and PolyBis-Tris

Two types of magnetic beads were used; control polystyrene magnetic beads (C) having a zwitterionic surface character and beads derivatised with Bis-Tris as described above (BT beads).

Each set receives one of five treatments. The polyBis-Tris used in each of the treatments was produced in a method as described in Example 1. Treatments were:

A) CONTROL: Treatment with PB/100 pH4.0 at 1 ml of 1 mg/ml Beads.

B) PAA: Treatment with polyacrylic acid (PAA) (240,000 M.Wt. Supplier: Aldrich) 0.1% w/w in PB/100 pH4.0.

C) PT: Treatment with polyBis-Tris (PT) 1 ml at 1 mg/ml in PB/100 pH4.0

D) PT/PAA: Treatment with polyBis-Tris (PT) as in (C) followed by a wash in PB/100 and PAA treatment as in (B).

E) PAA/PT: PAA treatment as in (B), followed by a wash in PB/100 and treatment with polyBis-Tris as in (C).

Four replicate samples were prepared for each of the control or BT-derivatised sets receiving treatments A, B, C, D and E.

Example 7

DNA Binding and Elution

After two washes with PB/100 buffer, DNA binding and elution was carried out on 1 mg amounts of both bead types produced in Example 6.

DNA binding and release was carried out by exposing 1 mg starting amount of bead to 1 ml of 50 µg/ml of Calf thymus genomic DNA (Sigma D-1501 Lot 11K7025) in DW. The beads were incubated for 5 minutes, washed with 2 changes of PB/100 pH5, then 200 µl of elution buffer. DNA yields were calculated from spectroscopy and OD ratio at 260/280 nm.

The average yields for control beads were: A) Control 3.74+/−0.15 se µg/mg, B) Core-PAA 2.62+/−0.35 se µg/mg, C) Core-PT 7.95+/−0.38 se µg/mg, D) Core-PT-PAA 2.63+/−0.17 se µg/mg, E) Core-PAA-PT 11.57+/−0.36 se µg/mg.

The average yields for the Bis-Tris coupled beads (BT) were: A) BT-Control 3.24+/−0.16 sse µg/mg, B) BT-PAA 3.40+/−0.19 se µg/mg, C) BT-PT 4.51+/−0.16 se µg/mg, D) BT-PT-PAA 2.89+/−0.21 se µg/mg, E) BT-PAA-PT 10.38+/−0.52 se µg/mg.

Figure 4:
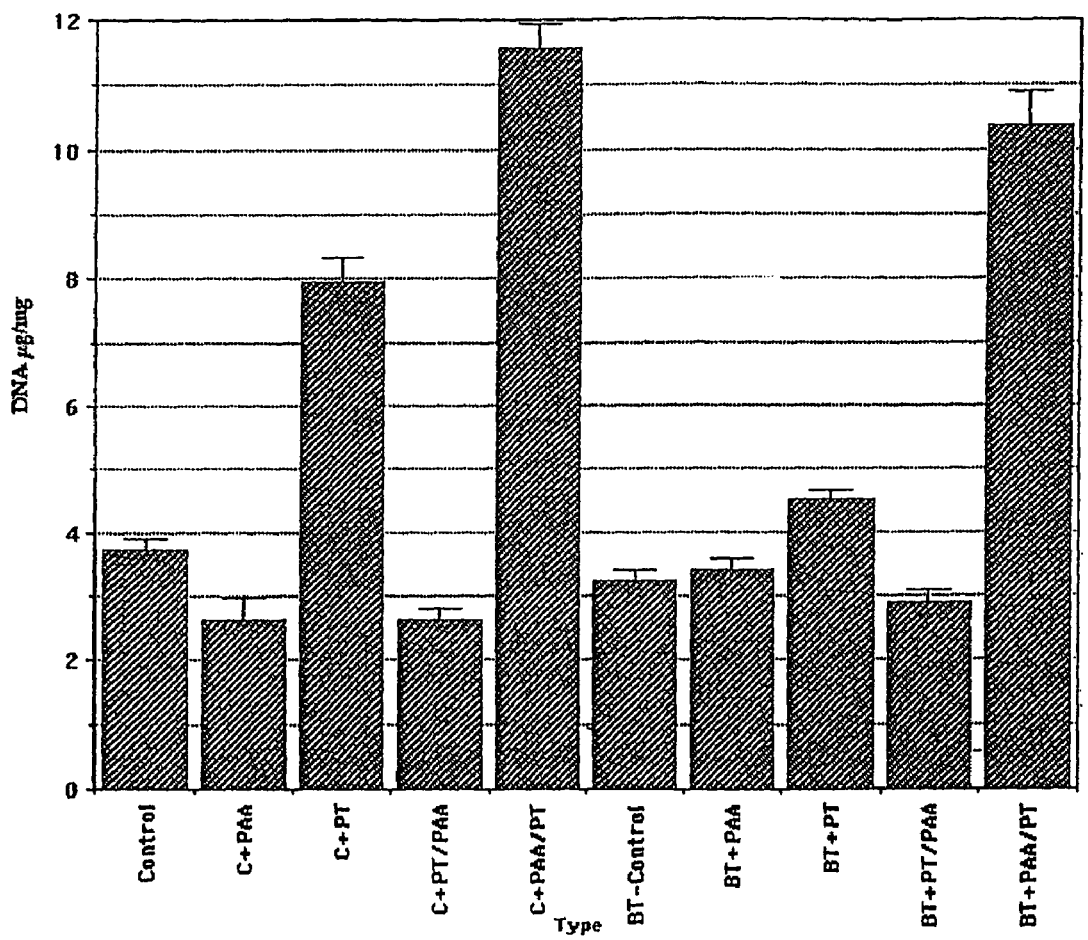
FIG. 4 shows the yield of DNA produced by elution from zwitterionic control beads and Bis-Tris derivatized beads, having a various number of layers of polyacrylic acid (PAA) and/or polyBis-Tris (PT).

These results are shown in FIG. 4.

It can be seen that a surface layer of polyBis-Tris (i.e., a layer that is positively charged at the first pH) is needed for DNA binding, but an undercoat of PAA can improve the binding capacity and increase the proportion of DNA recovered in the elution.

Example 8

Dye Binding and Elution

In this example, dye molecules are used to demonstrate the feasibility of binding and eluting small molecules such a pharmaceuticals from carriers of the invention. Two dyes are used, Congo Red (which is anionic at low pH) and Neutral Red (which is cationic at low pH).

An aqueous solution of 1 mM Congo Red or Neutral Red was added at 1 ml volume to a 1 mg sample of each of the beads described in Example 6. Binding was carried out at pH 5 in a dilute potassium acetate/potassium chloride (10/7 mM) buffer for 1 hour, and the beads were washed.

Elution of the dyes was carried out in 200 microlitres of Elution buffer comprising 10 mM Tris HCl. A second and final elution at low pH 1-2 was carried out for the cationic Neutral Red dye alone.

The resulting eluents were removed from contact with the beads. The eluent was pH corrected to a low pH for Neutral Red and a high pH for Congo Red by 1:1 dilution with 10 mM HCl or NaOH respectively, and their concentration determined by spectrophotometry at 525 and 495 nm respectively against a 0.1 mM standard.

The average single elution yields of the Congo Red at high pH, and Neutral Red at low pH, for the Control and Poly Bis-Tris coupled beads are given below:

The average yields for anionic Congo Red on control beads were: A) Control 75.3+/−1.1 nM/mg, B) Core-PAA 3.0+/−0.3 se nM/mg, C) Core-PT 71.7+/−4.9 se nM/mg, D) Core-PT-PAA 79.3+/−1.2 nM/mg, E) Core-PAA-PT 72.6+/−1.1 se nM/mg.

The average yields for anionic Congo Red on the BisTris coupled beads (BT) were: A) BT Control 82.2+/−4.7 se nM/mg, B) BT-PAA 13.4+/−0.1 se nM/mg, C) BT-PT 77.0+/−2.8 se nM/mg, D) BCore-PT-PAA 32.4+/−1.0 se nM/mg, E) BT-PAA-PT 68.4+/−1.1 se nM/mg.

The yields after elution at low pH for cationic Neutral Red on control beads were: A) Core 11.7+/−0.3 nM/mg, B) Core-PAA 13.4+/−0.1 se nM/mg, C) Core-PT 4.2+/−0.1 se nM/mg, D) Core-PT-PAA 13.3+/−0.4 se nM/mg, E) Core-PAA-PT 6.9+/−0.1 se nM/mg.

The yields after elution at low pH for cationic Neutral Red on the BisTris coupled beads (BT) were: A) BT Control 1.5+/−0.2 se nM/mg, B) BT-PAA 12.9+/−0.9 se nM/mg, C) BT-PT 1.4+/−0.2 se nM/mg, D) BT-PT-PAA 13.8+/−0.1 se nM/mg, E) BT-PAA-PT 6.8+/−0.9 se nM/mg.

Figure 5:
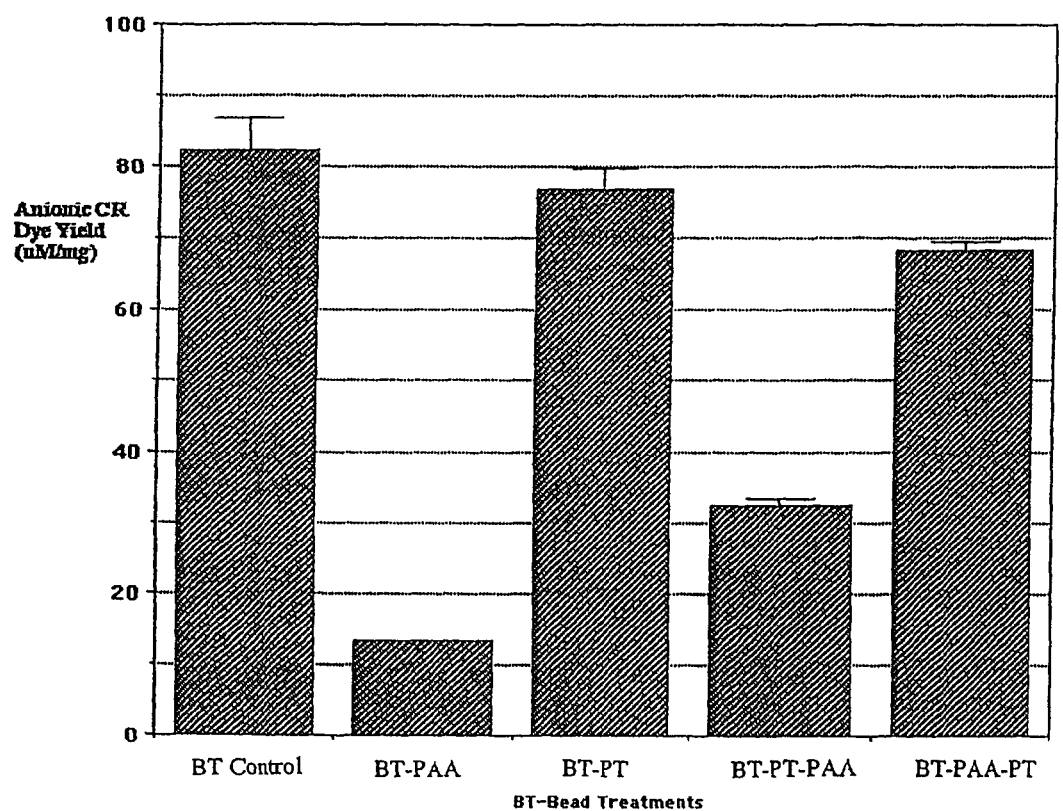
FIG. 5 shows the yield of anionic dye produced by elution from zwitterionic control beads (C) and Bis-Tris derivatized beads (BT), having a various number of layers of polyacrylic acid (PAA) and/or polyBis-Tris (PT).

The results for Congo Red on Bis-Tris coupled beads are shown in FIG. 5. It can be seen that good yields are achieved by binding to a cationic surface, including the cationic surface of multilayer beads.

These results demonstrate that a small bioactive molecule analogue can be bound at an intermediate pH, after particle synthesis, and eluted either at a higher or lower pH according to the prevailing polarity of the bound molecule. Furthermore different layers and ordering of binding of polymer provide control of the binding and elution yield of the analogue.

Example 9

Formation of Spherotech Beads with Multiple Layers of PolyBis-Tris and PolyAcrylic Acid Spherotech Beads (large magnetic polystyrene beads with an amine surface) receive one of five treatments before DNA binding and elution. The polyBis-Tris used in this example was produced in a method as described in example 2. The treatments were:

A) CONTROL: Treatment with precipitation Buffer (1/100 strength) pH5.0.

B) PAA: Treatment with PAA—0.1% w/w Polyacrylic Acid (240 k M.Wt. Sigma) in PB/100 pH 5.0.

C) PT: Treatment with polyBis-Tris (PT)—PolyBis-Tris used at 1 mg/ml in PB/100 pH 5.0.

D) PAA/PT: Treatment with PAA at 0.1% w/w as in (B) followed by a wash step of PB/100 pH5, and then treatment with polyBis-Tris as in (C)

E) PAA/PT/PAA/PT: Treatment as in (D) to give a PAA/PT base followed by a PB/100 pH5 wash, then PAA treatment as in (ii) and then a further PB/100 pH 5 wash and final polyBis-Tris treatment as in (C), to give a double layer cycle.

Example 10

DNA Binding and Elution

DNA binding and release was carried out by exposing a 1 mg starting amount of each resultant bead to 1 ml of 50 µg/ml of Calf thymus genomic DNA (Sigma D-1501 Lot 11K7025) in pH 5.0 PB/100. The beads were incubated for 5 minutes, washed with 2 changes of PB/100 pH5, then 200 µl of elution buffer. DNA yields were calculated from spectroscopy and OD ratio at 260/280 nm.

The mean DNA elution yields were (A) Core Bead 0.52+/−0.06 se µg/mg, (B) Core-PAA 0.57+/−0.20 se µg/mg, (C) Core-PT 2.39+/−0.04 se µg/mg (D) Core-PAA-PT 3.84+/−0.10 se µg/mg, (E) Core-PAA-PT-PAA-PT 6.47+/−0.26 se µg/mg, where se is standard error.

Figure 6:
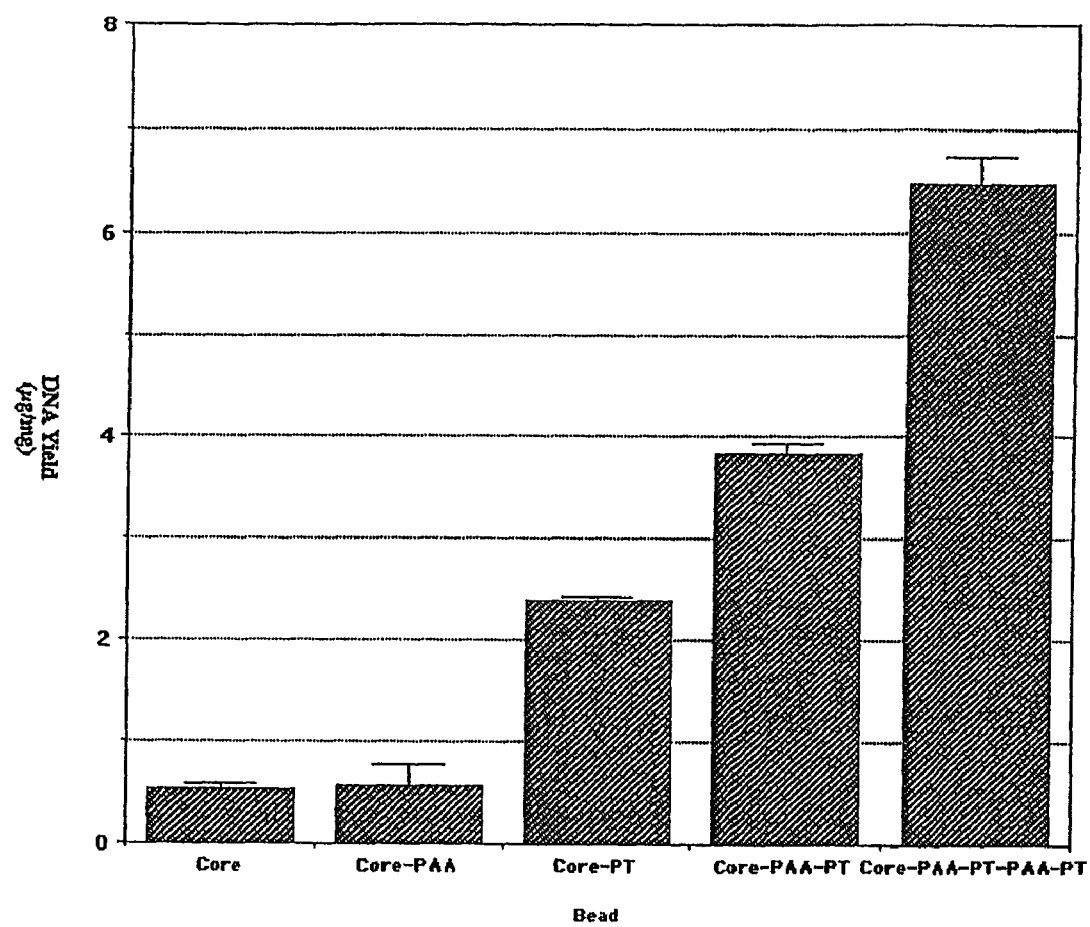
FIG. 6 shows the yield of DNA produced by elution from Spherotech beads having a various number of layers of polyacrylic acid and polyBis-Tris.

These yield are shown in FIG. 6. It can be seen that pre-treatment with PAA before PT (D) gives a synergistic increase in DNA binding compared to PT treatment alone (C). Moreover, if addition layers of PAA and polyBis-Tris are added, there is a further increase in the yield of DNA that can be obtained.

Example 11

Dye Binding and Elution

Each of the beads produced in Example 9 were contacted with 1 ml of 0.1 mM of Congo Red or Neutral Red in PB/100 at pH4.0 for one hour, and then washed with PB/100 pH4.

The dyes were released with 200 µl of elution buffer. The eluent for Neutral Red and Congo Red were corrected to low and high pH respectively, and dye release yields were calculated from spectrophotometry at 525 nm and 495 nm respectively.

Figure 7:
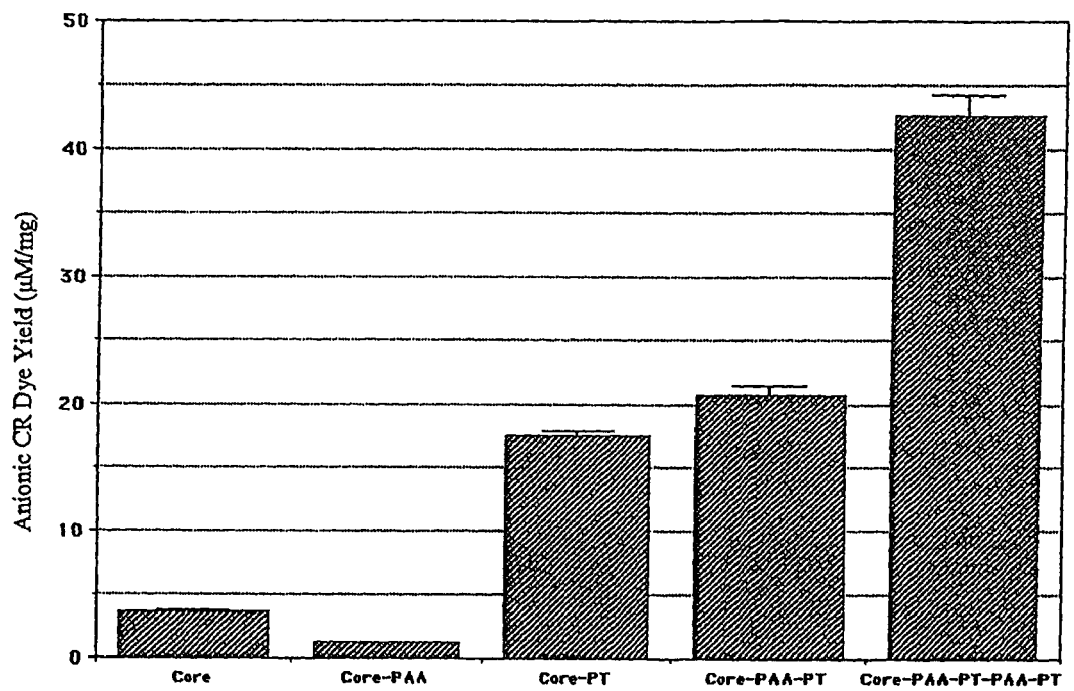
FIG. 7 shows the yield of anionic dye produced by elution from Spherotech beads having a various number of layers of polyacrylic acid and polyBis-Tris.

The yields of Congo Red dye (nominally anionic under acidic binding conditions) released at pH 8.5 were as follows:
(A) Core Bead 3.6+/−0.1 se nM/mg, (B) Core-PAA 1.2+/−0.0 se nM/mg, (C) Core-PT 17.5+/−0.3 se nM/mg (D) Core-PAA-PT 20.7+/−0.7 se nM/mg, (E) Core-PAA-PT-PAA-PT 42.7+/−1.6 se nM/mg, where se is standard error. These results are shown in FIG. 7.

The yields of Neutral Red dye (nominally cationic on binding) released at pH 8.5 were as follows:
(A) Core Bead 1.5+/−0.0 se nM/mg, (B) Core-PAA 2.6+/−0.1 se nM/mg, (C) Core-PT 1.1+/−0.0 se nM/mg (D) Core-PAA-PT 1.5+/−0.1 se nM/mg, (E) Core-PAA-PT-PAA-PT 9.9+/−0.7 se nM/mg, where se is standard error.

Figure 8:
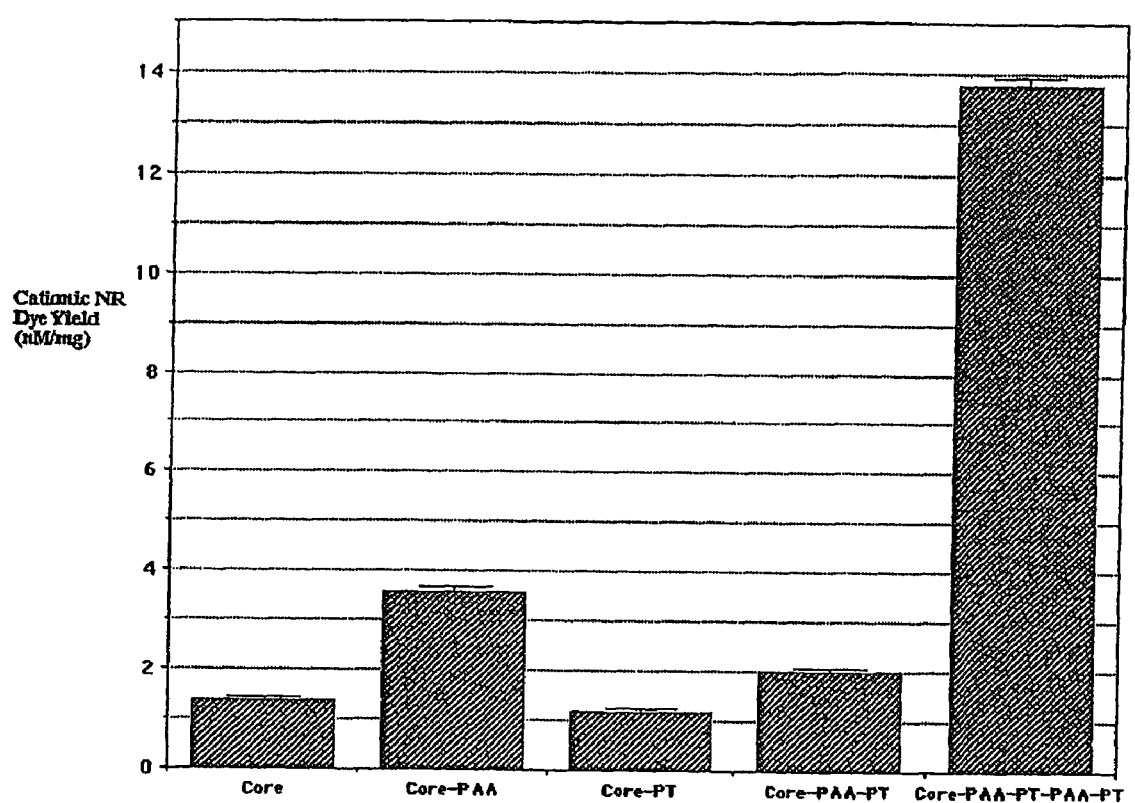
FIG. 8 shows the yield of cationic dye produced by elution at low pH from Spherotech beads having a various number of layers of polyacrylic acid and polyBis-Tris.

Elution of NR under low pH conditions (pH 1-2) gave a final release of (A) Core Bead 1.4+/−0.0 se nM/mg, (B) Core-PAA 3.6+/−0.1 se nM/mg, (C) Core-PT 1.1+/−0.1 se nM/mg (D) Core-PAA-PT 2.0+/−0.1 se nM/mg (E) Core-PAA-PT-PAA-PT 13.8+/−0.2 se nM/mg, where se is standard error. These results are shown in FIG. 8.

The dye binding results in this example demonstrate that a small bioactive molecule analogue can be bound at an intermediate pH, after particle synthesis, and eluted either at a higher or lower pH according to the prevailing polarity of the bound molecule. More alternate layers of polyion on the particle provide a greater binding and elution yield of the analogue.

Example 12

Multiple Layers of DNA With PolyBis-Tris

Bis-Tris derivatized beads received one of five treatments. The polyBis-Tris used in this example was produced in a method according to Example 1. The treatments were:
A) CONTROL: Treatment with precipitation buffer
B) DNA: Treatment with DNA. The DNA was Sigma D-1501, Lot 11K7025. Treatment was for 10 minutes, using 50 µl/ml in 1/100 precipitation buffer (PB) at pH4.0
C) DNA/PT: Treatment with DNA as in B) and then Poly-Bis-Tris at 25 mg/ml in pH4 PB/100.
D) DNA/PT/DNA: Treatment with DNA and PolyBis-Tris as in C) and then a second treatment with DNA as in B).
E) DNA/PT/DNA/PT: Treatment as in D) and then a second treatment with PolyBis-Tris at 25 mg/ml in pH4 PB/100.

Four replicates were carried out for each of the treatment types.

Example 13

DNA Binding and Elution

Each of the treatments groups produced in Example 12 were incubated in 1 ml of 50 µg/ml of Calf thymus genomic DNA in precipitation buffer 1/100 pH 4.0 to provide all treatments with a final DNA treatment.

After 2 washing steps, elution was carried out using 200 ul of elution buffer. The yield of DNA was measured from Optical Density at 260/280 nm.

DNA concentrations of a single elution were:
(A) 17.41+/−0.28 se µg/ml, (B) 18.35+/−0.44 se µg/ml, (C) 28.53+/−0.61 se µg/ml, (D) 44.2+/−1.31 se µg/ml, (E) 54.46+/−1.15 se µg/ml.

Figure 9:
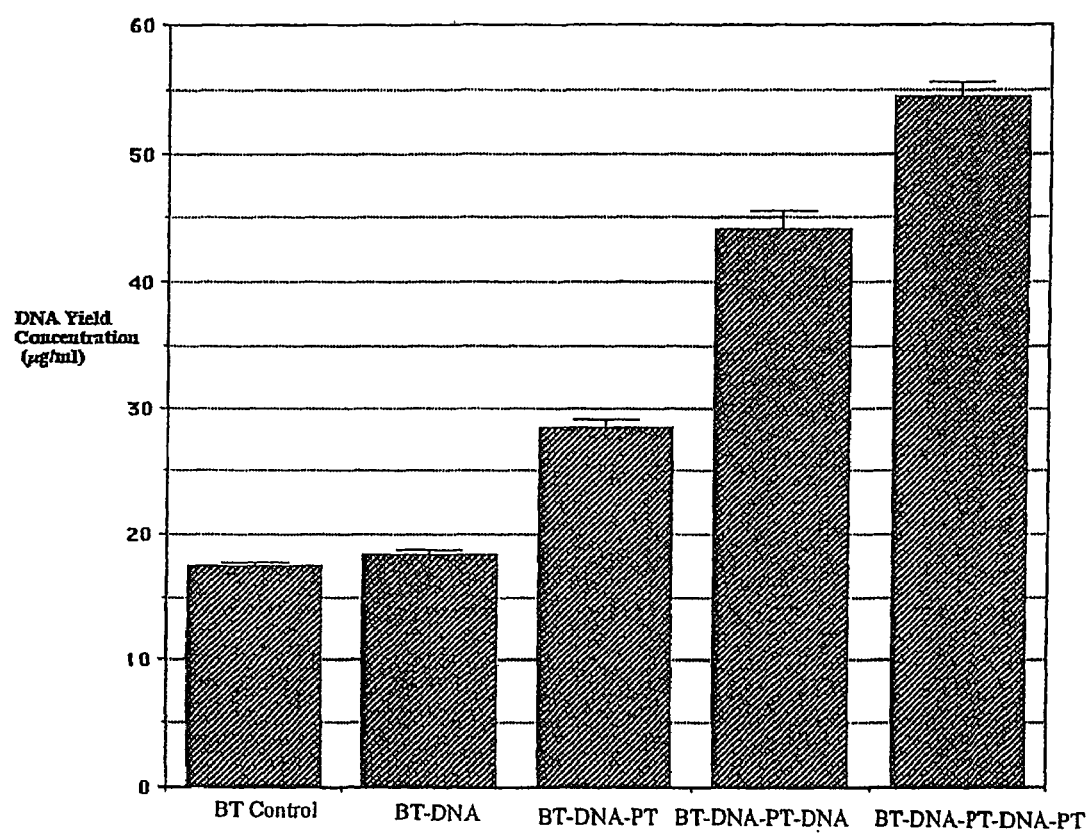
FIG. 9 shows the yield of DNA produced by elution from beads having a various number of layers of DNA and polyBis-Tris (PT).

These results are shown in FIG. 9. It can be seen that the yield increases as the number of layers increases, and is higher than in previous examples, which can be explained in part by the fact that DNA (the desired substance) is comprised in multiple layers.

It will be observed that example D gives a higher yield than example C, even though both have the same number of layers after treatment with DNA. This seems to be due to the full binding capacity for DNA not being exhausted after one round of exposure.

Example 14

Dye Binding and Elution

Approximately 1 mg of each bead type produced in example 12 was contacted with 1 ml of 0.1 mM Congo Red (CR) or Neutral Red (NR) in PB/100 at pH4.0. The beads were incubated in either of these dyes for 1 hour, then washed in PB/100 pH4.

The dyes were then released with 200 µl of Elution Buffer comprising 10 mM Tris HCl. The eluent containing Congo Red and Neutral Red, were corrected to high and low pH respectively. Dye release yields were calculated from spectrophotometry at 495 nm for CR and 525 nm for NR.

Figure 10:
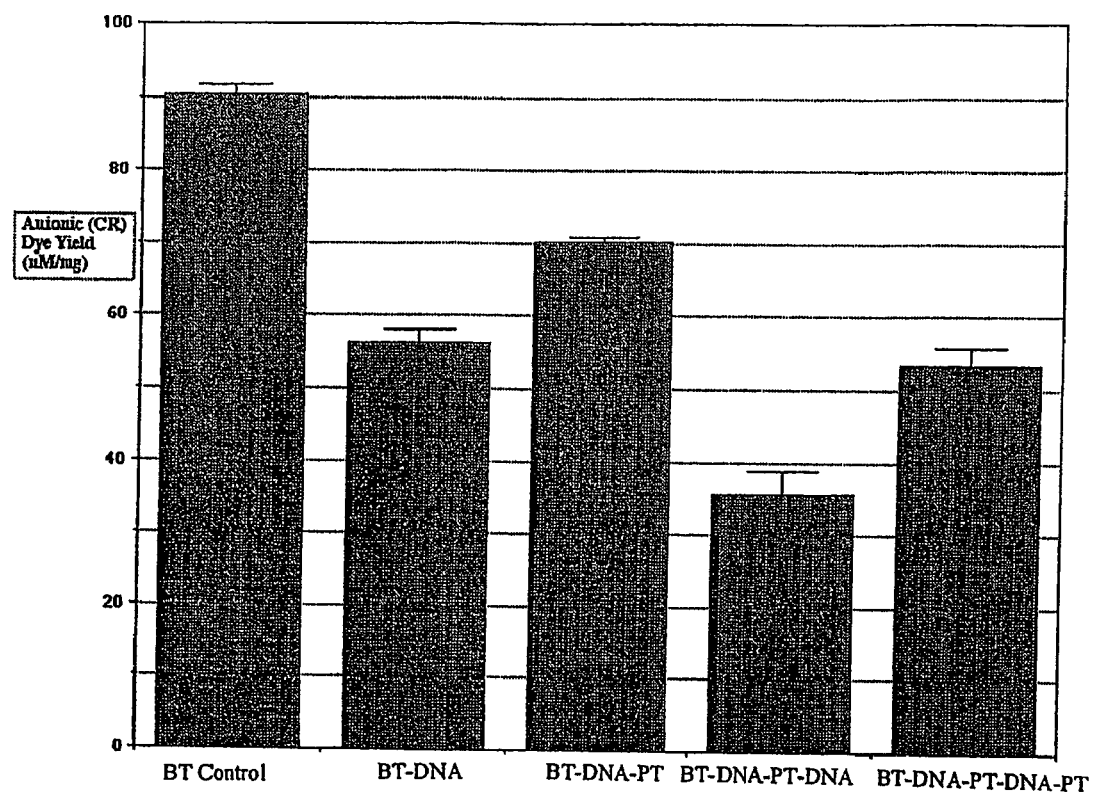
FIG. 10 shows the yield of anionic dye produced by elution from beads having a various number of layers of DNA and polyBis-Tris (PT).

The yields of Congo Red dye (nominally anionic on binding) released at pH 8.5 were as follows: (A) BT Control 90.4+/−1.4 se nM/mg, (B) BT-DNA 56.2+/−1.4 se nM/mg, (C) BT-DNA-PT 70.1+/−0.8 se nM/mg, (D) BT-DNA-PT-DNA 35.7+/−3.2 se nM/mg, (E) BT-DNA-PT1-DNA-PT 53.3+/−2.6 se nM/mg. The results are shown in FIG. 10.

The yields of Neutral Red dye (nominally cationic on binding) released at pH 8.5 were as follows:
(A) BT Control 1.1+/−0.1 se nM/mg, (B) BT-DNA 3.9+/−0.1 se nM/mg, (C) BT-DNA-PT 1.1+/−0.1 se nM/mg, (D) BT-DNA-PT-DNA 2.5+/−0.2 se nM/mg, (E) BT-DNA-PT-DNA-PT 1.1+/−0.0 se nM/mg.

Subsequent second elution of the NR at a low pH (pH 1-2) provided the following dye yields:
(A) BT Control 1.2+/−0.1 se nM/mg, (B) BT-DNA 9.3+/−0.3 se nM/mg, (C) BT-DNA-PT 1.4+/−0.3 se nM/mg, (D) BT-DNA-PT-DNA 1.0+/−0.1 se nM/mg, (E) BT-DNA-PT-DNA-PT 3.3+/−0.5 se nM/mg. These results are shown in FIG. 11.

These results demonstrate that a small bioactive molecule analogue can be bound at an intermediate pH, after synthesis of a particle comprised of PT and DNA, and eluted either at a higher (CR) or lower (NR) pH according to the prevailing polarity of the bound molecule.

These results also show that DNA as a polyanion can act as a binding substrate to carry a positively charged bioactive (here NR).

Abbreviations used in Examples 15 to 33
PT=PolyBis-Tris
PA=Polyacrylic Acid,
PAM=Polyallylamine,
DNA=Deoxyribonucleic acid
PL=GFP Plasmid [pCS2*mt-SGP]

Formation of Layered Poly Bis-Tris Coupled Beads for Examples 15-21
(A) 1 mg of Poly Bis-Tris coupled beads washed with 1 ml of PB1/100 pH 4.0.
(B) 1 mg of PolyBis-Tris coupled beads washed with 1 ml of PB1/100 pH 4.0. Layered with 200 µl of 0.1% Polyacrylic acid (240,000 mwt) and incubated for 5 minutes at room temperature. The beads were washed with 1 ml PB1/100 pH4.0.
(C) 1 mg of Bis-Tris coupled beads washed with 1 ml of PB1/100 pH 4.0. Layered with 200 µl of 0.1% Polyacrylic acid (240,00 mwt) and incubated for 5 mins at room temperature followed by 200 µl of 1 mg/ml PolyBis-Tris and incubated for 5 minutes at room temperature. The beads were washed with 1 ml PB1/100 pH 4.0.

Four replicate samples of the above treated bead types were prepared for each experiment. Treated bead types (A) and (C) above were used to bind and elute the following species.

Example 15

Folic Acid Binding and Elution

Folic acid is anionic and also known as Vitamin Bc. Folic acid is a representative member of the group of vitamins used in medicine, healthcare, agricultural, animal husbandry and food industries.

Folic acid (FA) binding and release was carried out by exposing 1 mg of each type of treated bead to 1 ml of 1 mg/ml folic acid in PB1/100 pH4.0. The beads were incubated for 5 minutes, washed with 1 ml PB1/100 pH4.0, then 200 µl of elution buffer. Folic acid yields were calculated from constructing a standard curve of folic acid using the absorbance at 275 nm.

The mean folic acid elution yields were:
(A) Bis-Tris: 3.178 µg/mg+/−0.276,
(B) Bis-Tris/PA: 8.748 µg/mg+/−5.32,
(C) Bis-Tris/PA/PT: 4.191 µg/mg+/−2.10,
(D) Bis-Tris/FA: 189.756 µg/mg+/−22.40,
(E) Bis-Tris/PA/PT/FA: 1306.816 µg/mg+/−94.93.

These findings show that a significant yield of folic acid is bound and eluted from the Bis-Tris coupled bead. This yield is increased on the layering of polyacrylic acid and PolyBis-Tris on the coupled magnetic bead.

Example 16

Salicylic Acid Binding and Elution

Salicylic acid is anionic and a precursor to aspirin. Salicylic acid represents a member of the group of analgesics and other pharmacological agents important in the pharmaceutical and healthcare industries.

Salicylic acid (SA) binding and release was carried out by exposing 1 mg of each type of treated bead to 1 ml of 2 mg/ml salicylic acid in PB1/100 pH4.0. The beads were incubated for 5 minutes, washed with 1 ml PB1/100 pH4.0, then 200 µl of elution buffer. Salicylic acid yields were calculated from constructing a standard curve of salicylic acid using the absorbance at 275 nm.

The mean salicylic acid elution yields were:
(A) Bis-Tris: 0.03 µg/mg+/−0.001,
(B) Bis-Tris/PA: 0.03 µg/mg+/−0.002,
(C) Bis-Tris/PA/PT: 0.042 µg/mg+/−0.001,
(D) Bis-Tris/SA: 3.37 µg/mg+/−0.21,
(E) Bis-Tris/PA/PT/SA: 8.90 µg/mg+/−1.06.

These findings show that a significant yield of salicylic acid is bound and eluted from the Bis-Tris coupled bead. This yield is increased on the layering of polyacrylic acid and Poly Bis-Tris on the coupled magnetic bead.

Example 17

Ampicillin Binding and Elution

Ampicillin is a zwitterionic and broad spectrum antibiotic. As a semi-synthetic derivative of penicillin it is a representative member of pharmaceutical and pharmacologically active range of agents.

Ampicillin (Amp) binding and release was carried out by exposing 1 mg of each type of treated bead to 1 ml of 10 mg/ml Ampicillin in PB1/100 pH4.0. The beads were incubated for 5 minutes, washed with 1 ml PB1/100 pH4.0, then 200 µl of elution buffer. Ampicillin yields were calculated from constructing a standard curve of salicylic acid using the absorbance at 255 nm.

The mean Ampicillin elution yields were:
(A) Bis-Tris: 34.40 µg/mg+/−1.09,
(B) Bis-Tris/PA: 39.08 µg/mg+/−1.48,
(C) Bis-Tris/PA/PT: 56.27 µg/mg+/−1.02,
(D) Bis-Tris/Amp: 85.96 µg/mg+/−2.34,
(E) Bis-Tris/PA/PT/Amp: 128.15 µg/mg+/−0.47.

These findings show that a significant yield of Ampicillin is bound and eluted from the Bis-Tris coupled bead. This yield is increased on the layering of polyacrylic acid and Poly Bis-Tris on the coupled magnetic bead.

Example 18

Abscisic Acid Binding and Elution

Abscisic acid is an organic acid and plant hormone, promoting abscission such as leaf drop. As a plant hormone it is a representative member of the group of botanical, horticultural and agriculturally active agents.

Abscisic acid (AA) binding and release was carried out by exposing 1 mg of each type of treated bead to 200 µl of PB1/100 pH4.0, 50 µl of 10 mg/ml Abscisic acid in 100 mM NaHCO$_3$. The beads were incubated for 5 minutes, washed with 1 ml PB1/100 pH4.0, then 200 µl of elution buffer. Abscisic acid yields were calculated from constructing a standard curve of Abscisic acid using the absorbance at 252 nm.

The mean Abscisic acid elution yields were:
(A) Bis-Tris: 1.038 mg/mg+/−0.034,
(B) Bis-Tris/PA: 1.403 mg/mg+/−0.007,
(C) Bis-Tris/PA/PT: 1.923 mg/mg+/−0.019,
(D) Bis-Tris/AA: 4.327 mg/mg+/−923.077,
(E) Bis-Tris/PA/PT/AA: 12.60 mg/mg+/−1.019.

These findings show that a significant yield of Abscisic acid is bound and eluted from the Bis-Tris coupled bead. This yield is increased on the layering of polyacrylic acid and Poly Bis-Tris on the coupled magnetic bead.

Example 19

Cetylpyridinium Chloride Binding and Elution

Cetylpyridinium Chloride is a cationic organic surfactant with uses as an antiseptic, disinfectant, topical ant-infective and preservative in pharmaceuticals. As such it is a representative member of the antibacterial and biocide agents used in medicine, veterinary, pharmaceutical, and various industries, including household and industrial cleaning products.

Cetylpyridinium Chloride (CC) binding and release was carried out by exposing 1 mg of each type of treated bead to 1 ml of 10 mg/ml Cetylpyridinium Chloride in PB1/100 pH4.0. The beads were incubated for 5 minutes, washed with 1 ml PB1/100 pH4.0, then 200 μl of 10 mM NaOH. Cetylpyridinium Chloride yields were calculated from constructing a standard curve of Cetylpyridinium Chloride using the absorbance at 255 nm.

The mean Cetylpyridinium Chloride elution yields were:
(A) Bis-Tris: 1.59 μg/mg+/−0.03,
(B) Bis-Tris/PA: 2.84 μg/mg+/−0.17,
(C) Bis-Tris/PA/PT: 4.90 μg/mg+/−0.11,
(D) Bis-Tris/CC: 2.78 μg/mg+/−0.27,
(E) Bis-Tris/PA/PT/CC: 8.83 μg/mg+/−0.46.

These findings show that a significant yield of Cetylpyridinium Chloride a positively charged molecule (Zeta potential +39.6 mV+/−1.3 at pH4.0) is bound and eluted from the Bis-Tris coupled bead. This yield is increased on the layering of polyacrylic acid and Poly Bis-Tris on the coupled magnetic bead.

Example 20

Albumin (Bovine) Binding and Elution at pH4.0 and pH6.5

Albumin is a globular protein and the major serum protein found in blood. As a representative member of the protein class of biochemicals which have importance as pharmaceutical components, cosmetic formulations, food stuffs, feeds and nutriceuticals in the agricultural, medical, biomedical, biotechnology, pharmaceutical, defense, cosmetics and food industries.

Albumin (Bovine) (Alb) binding and release was carried out by exposing 1 mg of each type of treated bead to 1 ml of 30 mg/ml Albumin in PB1/100 pH4.0. The beads were incubated for 5 minutes, washed with 1 ml PB1/100 pH4.0, then 200 μl of elution buffer. Albumin yields were calculated from constructing a standard curve of Albumin using the absorbance at 280 nm. This method was also conducted using PB1/100 pH6.5.

The mean Albumin elution yields bound at PB1/100 pH4.0 were:
(B) Bis-Tris/PA: 54.6 μg/mg+/−1.9,
(C) Bis-Tris/PA/PT: 109.1 μg/mg+/−7.0,
(D) Bis-Tris/Alb: 158.0 μg/mg+/−24.5,
(E) Bis-Tris/PA/PT/Alb: 1004.5 μg/mg+/−28.2.

These findings show that a significant yield of Albumin is bound at pH4.0 and eluted from the Bis-Tris coupled bead. This yield is increased on the layering of polyacrylic acid and Poly Bis-Tris on the coupled magnetic bead.

The mean Albumin elution yields bound at PB1/100 pH6.5 were:
(B) Bis-Tris/PA: 60.2 μg/mg+/−2.8,
(C) Bis-Tris/PA/pT: 176.8 μg/mg+/−3.2,
(D) Bis-Tris/Alb: 41.4 μg/mg+/−4.0,
(E) Bis-Tris/PA/PT/Alb: 423.2 μg/mg+/−1.1.

These findings show that a significant yield of Albumin is bound at pH6.5 and eluted from the Bis-Tris coupled bead. This yield is increased on the layering of polyacrylic acid and Poly Bis-Tris on the coupled magnetic bead.

Due to the multivalent nature of the albumin protein, a polyacrylic acid and Poly Bis-Tris layered bead can bind and elute albumin at pH4.0 and pH6.5. The Zeta potential of albumin is 3.3 MV+/−0.9 in PB1/100 pH4.0 and 0.9+/−0.9 PB1/100 pH6.5.

Example 21

Double Binding and Release of Genomic DNA and Salicylic Acid

This example combines the release of salicylic acid as an analgesic or drug precursor, and DNA as a therapeutic, transfection or diagnostic agent for combined release systems, that have utility in the medicine, biomedical, biotechnology, pharmaceutical, agriculture, horticulture, fisheries, and animal husbandry industries.

This example shows that two different substances can be eluted from multi-layered beads at subsequently higher pH values. Genomic calf thymus DNA and salicylic acid bind and release was conducted using multi-layered carboxylated magnetic beads.

Formation of the multi-layered beads for the double release of genomic DNA and salicylic acid:
(A) 1 mg of carboxylated magnetic beads washed with 1 ml of PB1/100 pH4.0.
(B) 1 mg of carboxylated magnetic beads layered with 200 μl of 20 mg/ml Polyallylamine hydrochloride in PB1/100 pH4.0, incubated for 5 minutes and washed with 1 ml of PB1/100 pH4.0.
(C) 1 mg of carboxylated magnetic beads layered with 200 μl of 20 mg/ml Polyallylamine hydrochloride (15,000 m.wt.) in PB1/100 pH4.0, incubated for 5 minutes, layered with 1 ml of 50 μg/ml of calf thymus genomic DNA and washed with 1 ml of PB1/100 pH4.0.
(D) 1 mg of carboxylated magnetic beads layered with 200 μl of 20 mg/ml Polyallylamine hydrochloride in PB1/100 pH4.0, incubated for 5 minutes, layered with 1 ml of 50 μg/ml of calf thymus genomic DNA, 200 μl of 1 mg/ml of Poly Bis-Tris in PB1/100 pH4.0, incubated for 5 minutes and washed with 1 ml of PB1/100 pH4.0.
(E) 1 mg of carboxylated magnetic beads layered with 200 μl of 20 mg/ml Polyallylamine hydrochloride in PB1/100 pH4.0, incubated for 5 minutes, layered with 1 ml of 50 μg/ml of calf thymus genomic DNA, 200 μl of 1 mg/ml of Poly Bis-Tris in PB1/100 pH4.0, incubated for 5 minutes, 1 ml 2 mg/ml salicylic acid in PB1/100 pH4.0, incubated for 5 minutes and washed with 1 ml of PB1/100 pH4.0.

The treated beads (A-E) were washed with 1 ml PB1/100 pH4.0, 200 μl of elution buffer, then 200 μl 10 mM NaOH. Salicylic acid yields were calculated from constructing a standard curve of salicylic acid using the absorbance at 300 nm and genomic DNA measured at 260 nm.

The mean salicylic acid elution yields from the first elute were:
(A) Bis-Tris/PAM: 0.05 μg/mg+/−0.00,
(B) Bis-Tris/PAM/DNA: 0.05 μg/mg+/−0.00,
(C) Bis-Tris/PAM/PT: 0.06 μg/mg+/−0.01,
(D) Bio-Tris/PAM/PT/SA: 1.09 μg/mg+/−0.06.

These findings show that a significant yield of salicylic acid is bound and eluted from the multi-layered bead. DNA yields from the first elution were all below 0.1 μg/mg and confirmed by agarose gel electrophoresis.

The mean DNA yields from the second elute were:
(A) Bis-Tris/PAM: 0.27 μg/mg+/−0.04,
(B) Bis-Tris/PAM/DNA: 0.90 μg/mg+/−0.91,
(C) Bis-Tris/PAM/PT: 8.65 μg/mg+/−1.23,
(D) Bis-Tris/PAM/PT/SA: 7.45 μg/mg+/−0.70.

Agarose gel electrophoresis was used to determine the presence of DNA in the elutions.

Example 22

Neutral Red Binding and Elution

Neutral Red is a zwitterionic dye that is cationic at low pH, and is a representative example of that group of cationic molecules that comprise a large proportion of materials and active agents such as drugs and pesticides. In this example Neutral Red is used to demonstrate the binding and release of a cationic molecule from a multi-layered bead.

Formation of the multi-layered beads for Neutral Red bind and release:
(A) 1 mg of Poly Bis-Tris coupled beads washed with 1 ml of PB1/100 pH 4.0.
(B) 1 mg of Poly Bis-Tris coupled beads washed with 1 ml of PB1/100 pH 4.0. Layered with 200 μl of 0.1% Polyacrylic acid (240,000 MWT) and incubated for 5 minutes at room temperature. The beads were washed with 1 ml PB1/100 pH4.0.
(C) 1 mg of Bis-Tris coupled beads washed with 1 ml of PB1/100 pH 4.0. Layered with 200 μl of 0.1% Polyacrylic acid (240,00 mwt) and incubated for 5 mins at room temperature followed by 200 μl of 1 mg/ml Poly Tris and incubated for 5 minutes at room temperature. The beads were washed with 1 ml PB1/100 pH4.0.
(D) 1 mg of Bis-Tris coupled beads washed with 1 ml of PB1/100 pH 4.0. Layered with 200 μl of 0.1% Polyacrylic acid (240,00 mwt) and incubated for 5mins at room temperature followed by 200 μl of 1 mg/ml Poly Tris and incubated for 5 minutes at room temperature and then a final layer of 200 μl of 0.1% Poly-acrylic acid as previous layer. The beads were washed with 1 ml PB1/100 pH4.0.

An aqueous solution of 0.1 mM Neutral Red was added at 1 ml volume to a 1 mg sample of each of the beads described above (A-D). Binding was carried out in PB1/100 at pH4.0 for 1 hour and the beads washed in PB1/100 pH4.0.

Neutral Red dye was eluted in 200 μl of elution buffer and then 200 μl of 1% w/w HCl. The resulting elutions were corrected to a low pH using 1% HCl and there concentration determined by spectrophotometry at 492 nm against a 0.1 mM standard.

The average yields of cationic Neutral Red were:
(A) Bis-Tris/NR: 9.56 nM/mg+/−0.91,
(B) Bis-Tris/PA/NR: 10.23 nM/mg+/−0.27,
(C) Bis-Tris/PA/PT/NR: 10.50 nM/mg+/−1.42,
(D) Bis-Tris/PA/PT/PA/NR: 37.61 nM/mg+/−10.73.

These results demonstrate that the multi-layering of PA/PT/PA to a Bis-Tris coupled bead significantly increases the yield of binding and elution of a cationic molecule.

Example 23

Carboxymethylcellulose Binding and Elution

Carboxymethylcellulose (here as a sodium salt) is an anionic polyion used as a thickening agent and viscosity enhancer in many foodstuffs, paints, adhesives, inks and pharmaceutical formulations, and is a characteristic member of such natural, semi-synthetic and synthetic polymers found in the food, chemical, agricultural and pharmaceutical industries. Binding and elution is measured indirectly is this instance using the zeta potential as a measure of surface charge to indicate polyion binding and release.

This experiment shows the change in the surface of a Bis-Tris coupled bead on bind and release of carboxymethylcellulose (CMC). Carboxymethylcellulose (CMC) binding and release was carried out by exposing 1 mg of each type of treated bead (A-C).
(A) 1 mg of Poly Bis-Tris coupled beads washed with 1 ml of PB1/100 pH 4.0.
(B) 1 mg of Poly Bis-Tris coupled beads washed with 1 ml of PB1/100 pH 4.0. Layered with 200 μl of 0.1% Polyacrylic acid (240,000 MWT) and incubated for 5 minutes at room temperature. The beads were washed with 1 ml PB1/100 pH4.0.
(C) 1 mg of Bis-Tris coupled beads washed with 1 ml of PB1/100 pH 4.0. Layered with 200 μl of 0.1% Polyacrylic acid (240,00 mwt) and incubated for 5 mins at room temperature followed by 200 μl of 1 mg/ml Poly Bis-Tris and incubated for 5 minutes at room temperature. The beads were washed with 1 ml PB1/100 pH4.0.

To each of the treated bead types (A-C), 200 μl ml of 0.25% w/w of carboxymethylcellulose in PB1/100 pH4.0 was added and incubated for 5 minutes, washed with 1 ml PB1/100 pH4.0 and the zeta potential measured. The treated beads were then washed with 200 μl of elution buffer and the zeta potential measured. The zeta potential of a Bis-Tris coupled bead +23.8 mV+/−0.2 (positive).

The following results show the zeta potential of the treated beads are treatment with carboxymethylcellulose:
(A) Bis-Tris/CMC: −23.4+/−0.8,
(B) Bis-Tris/PA/CMC: −21.2 mV+/−0.7,
(C) Bis-Tris/PA/PT/CMC: −20.0 mV+/−0.9.

These findings illustrate that similar amounts of totals of polyanion are bound to A, B and C, as indicated by the shift from positive to negative zeta potential (c. 20 mV) with respect to the positive charge of the control bead (+23 mV).

The zeta potential of the treated bead types after elution of carboxymethylcellulose are as follows:
(B) Bis-Tris/CMC: −8.2 mV+/−1.4,
(C) Bis-Tris/PA/CMC: −18.2 mV+/−0.7,
(D) Bis-Tris/PA/PT/CMC: +6.6 mV+/−0.5.

These findings show that the PA/PT/CMC bead after elution has a more positive zeta potential and shows the greatest change (C) [Change of −20.0 mV to +6.6 mV=+26.6 mV] compared with (A) [Change +15.2 mV] and B [Change +3.0 mV] and therefore significantly more carboxymethylcellulose is eluted from the PA/PT/CMC bead.

Example 24

Multilayering of DNA and Either PolyBis-Tris or Polyallylamine Hydrochloride

The example shows the binding and release of DNA on multi-layered on magnetic particles with Poly Bis-Tris and DNA or Polyallylamine hydrochloride and DNA PolyBis-Tris and Polyallylamine are two polycationic polymers. Polyallylamine has uses elsewhere as a binding agent that finds use in a variety of chemical and biological applications and industries.

DNA binding and release was carried out by exposing 1 mg of each type of treated bead to multi-layers of Poly Bis-Tris and calf thymus genomic DNA. The treatments for this experiment are as follows:
(A) 1 mg of Poly Bis-Tris coupled beads washed with 1 ml of PB1/100 pH 5.0.
(B) 1 mg of Bis-Tris coupled beads washed with 1 ml of PB1/100 pH 5.0. Layered with 1 ml of 0.1% Poly-acrylic acid (240,00 mwt) and incubated for 5 mins at room temperature followed by 200 µl of 1 mg/ml PolyBis-Tris and incubated for 5 minutes at room temperature. The beads were washed with 1 ml PB1/100 pH5.0.
(C) 1 mg of Bis-Tris coupled beads washed with 1 ml of PB1/100 pH 5.0. Layered with 1 ml of 0.1% Poly-acrylic acid (240,00 mwt) and incubated for 5 mins at room temperature followed by 200 µl of 1 mg/ml Poly Bis-Tris and incubated for 5 minutes at room temperature. Calf thymus genomic DNA 1 ml was added (50 µg/ml) in PB1/100 pH5.0, incubated 5 minutes and beads washed with 1 ml PB1/100 pH5.0.
(D) As (C) above with one outer layer of 200 µl of 1 mg/ml Poly Bis-Tris followed by 1 ml of 50 µg/ml calf thymus genomic DNA in PB1/100 pH 5.0, incubated 5 minutes and washed with 1 ml PB1/100 pH5.0.
(E) As (C) above with two outer layers of 200 µl of 1 mg/ml Poly Bis-Tris followed by 1 ml of 50 µg/ml calf thymus genomic DNA in PB1/100 pH 5.0, incubated 5 minutes and washed with 1 ml PB1/100 pH5.0.
(F) As (C) above with three outer layers of 200 µl of 1 mg/ml Poly Bis-Tris followed by 1 ml of 50 µg/ml calf thymus genomic DNA in PB1/100 pH 5.0, incubated 5 minutes and washed with 1 ml PB1/100 pH5.0.

A second set of treated magnetic beads were layered as above treatments (B-F) with 200 µl of 1 mg/ml of Polyallylamine hydrochloride in PB1/100 pH 5.0 replacing the layers of Poly Bis-Tris (G-K). All treatments were exposed to 200 µl of elution buffer and 200 µl of 10 mM NaOH. The elutes were analysed by agarose gel electrophoresis.

The mean concentration of DNA in the first elute for each of the treatments is as follows:
(A) Bis-Tris: 0.23 µg/mg+/−0.03,
(B) Bis-Tris/PA/PT: 0.45+/−0.16,
(C) Bis-Tris/PA/PT/DNA: 2.42+/−0.68,
(D) Bis-Tris/PA/PT/DNA/PT/DNA: 7.44 µg/mg+/−0.26,
(E) Bis-Tris/PA/PT/DNA/PT/DNA: 7.82 µg/mg+/−0.123,
(F) Bis-Tris/PA/PT/DNA/PT/DNA/PT/DNA: 8.65 µg/mg+/−0.945,
(G) Bis-Tris/PA/PAM: 0.42 µg/mg+/−0.03,
(H) Bis-Tris/PA/PAM/DNA: 0.68+/−0.02,
(I) Bis-Tris/PA/PAM/DNA/PAM/DNA: 0.28 µg/mg+/−0.13,
(J) Bis-Tris/PA/PAM/DNA/PAM/DNA: 0.33 µg/mg+/−0.111,
(K) Bis-Tris/PA/PAM/DNA/PAM/DNA/PAM/DNA: 0.37 µg/mg+/−0.151.

These findings show that in the treatments with increasing layers of Poly Bis-Tris and DNA, an increase in the concentration of DNA eluted is observed. The beads treated with alternating layers of Polyallylamine and DNA show minimal DNA elution when exposed to elution buffer.

The mean concentration of DNA in the second elute for each of the treatments is as follows:
(A) Bis-Tris: 0.76 µg/mg+/−0.19,
(B) Bis-Tris/PA/PT: 0.62+/−0.04,
(C) Bis-Tris/PA/PT/DNA: 0.92+/−0.02,
(D) Bis-Tris/PA/PT/DNA/PT/DNA: 1.09 µg/mg+/−0.05,
(E) Bis-Tris/PA/PT/DNA/PT/DNA: 0.91 µg/mg+/−0.02,
(F) Bis-Tris/PA/PT/DNA/PT/DNA/PT/DNA: 0.98 µg/mg+/−0.117,
(G) Bis-Tris/PA/PAM: 0.85 µg/mg: +/−0.03,
(H) Bis-Tris/PA/PAM/DNA: 2.54+/−0.13,
(I) Bis-Tris/PA/PAM/DNA/PAM/DNA: 3.57 µg/mg+/−0.12,
(J) Bis-Tris/PA/PAM/DNA/PAM/DNA: 4.96 µg/mg+/−2.739,
(K) Bis-Tris/PA/PAM/DNA/PAM/DNA/PAM/DNA: 13.60 µg/mg+/−2.024.

These findings show that in the treatments with alternating layers of Polyallylamine hydrochloride and DNA, the DNA is eluted in the second elution, a higher pH than the layers of Poly Bis-Tris and DNA. The concentration of DNA in second elute, increases with increasing layers of Polyallylamine hydrochloride and DNA.

Example 25

Multi-Layering of Poly Bis-Tris, DNA and Polyethyleneimine DNA Binding and Elution The example shows the binding and release of DNA on multi-layered carboxylated magnetic particles with DNA and Polyethyleneimine. Polyethyleneimine is a cationic polymer with a variety of uses as a binding agent in various industries.

DNA binding and release was carried out by exposing 1 mg of each type of treated bead to multi-layers of Polyethylenieimine (70K mwt) (PEI) and calf thymus genomic DNA. The treatments for this experiment are as follows:
(A) 1 mg of Poly Bis-Tris coupled beads washed with 1 ml of PB1/5 pH 5.0.
(B) 1 mg of Bis-Tris coupled beads washed with 1 ml of PB1/5 pH 5.0. Layered with 1 ml of 0.1% Poly-acrylic acid (240,00 mwt) and incubated for 5 mins at room temperature followed by 200 µl of 1 mg/ml Poly Tris and incubated for 5 minutes at room temperature. The beads were washed with 1 ml PB1/5 pH5.0.
(C) 1 mg of Bis-Tris coupled beads washed with 1 ml of PB1/5 pH 5.0. Layered with 1 ml of 0.1% Poly-acrylic acid (240,00 mwt) and incubated for 5 mins at room temperature followed by 200 µl of 1 mg/ml Poly Tris and incubated for 5 minutes at room temperature. Calf thymus genomic DNA 1 ml was added (50 µg/ml) in PB1/100 pH5.0, incubated 5 minutes and beads washed with 1 ml PB1/5 pH5.0.
(D) As (C) above with one outer layer of 1 ml of 1 mg/ml Polyethyleneimine followed by 1 ml of 50 µg/ml calf thymus genomic DNA in PB1/5 pH 5.0, incubated 5 minutes and washed with 1 ml PB1/5 pH5.0.
(E) As (C) above with two outer layers of 1 ml of 1 mg/ml Polyethyleneimine followed by 1 ml of 50 µg/ml calf thymus genomic DNA in PB1/5 pH 5.0, incubated 5 minutes and washed with 1 ml PB1/5 pH5.0.
(F) As (C) above with three outer layers of 1 ml of 1 mg/ml Polyethyleneimine followed by 1 ml of 50 µg/ml calf thymus genomic DNA in PB1/5 pH 5.0, incubated 5 minutes and washed with 1 ml PB1/5 pH5.0.

All treatments were exposed to 200 µl of elution buffer and 200 µl of 10 mM NaOH. The concentration of DNA was measured at 260 nm and eluate analysed by agarose gel electrophoresis.

The mean concentration of DNA in the first elution for each of the treatments is as follows:
(A) Bis-Tris: 4.43 µg/mg+/−1.39,
(B) Bis-Tris/PA/PT: 5.69+/−0.33,
(C) Bis-Tris/PA/PT/DNA: 46.76+/−0.38,
(D) Bis-Tris/PA/PT/DNA/PEI/DNA: 4.04 µg/mg+/−0.51,
(E) Bis-Tris/PA/PT/DNA/PEI/DNA/PT/DNA: 6.88 µg/mg+/−0.273,
(F) Bis-Tris/PA/PT/DNA/PEI/DNA/PT/DNA/PEI/DNA: 2.44 µg/mg +/−0.036.

The mean concentration of DNA in the second elution for each of the treatments is as follows:
(A) Bis-Tris: 5.69 µg/mg+/−0.29,
(B) Bis-Tris/PA/PT: 3.94+/−0.39,
(C) Bis-Tris/PA/PT/DNA: 11.18+/−0.18,
(D) Bis-Tris/PA/PT/DNA/FEI/DNA: 61.86 µg/mg+/−5.71,
(E) Bis-Tris/PA/PT/DNA/PEI/DNA/PT/DNA: 84.09 µg/mg+/−4.108,
(F) Bis-Tris/PA/PT/DNA/PEI/DNA/PT/DNA/PEI/DNA: 33.91 µg/mg+/−5.922.

Thus, (C) with PA/PT/DNA gives the largest first elution yield of 47 µg/mg and in the second elute this is eclipsed by (E) with PA/PT/DNA/PEI/DNA/PT/DNA layers gave a 84 µg/mg release.

Example 26

Insulin Binding and Elution

Insulin is a polypeptide and endocrine hormone found in vertebrates that regulates carbohydrate metabolism. Insulin is a representative member of the group of natural and synthetic hormones, bioactive peptides and biological peptide agents and analogs important in the biochemical, biomedical, veterinary and pharmaceutical fields.

Insulin (IN) binding and release was carried out by exposing 1 mg of each two types of treated bead to 1 ml of 500 µg/ml insulin in PB1/100 pH4.0. These were:
A) 1 mg of Bis-Tris coupled magnetic polystyrene bead washed with 1 ml of PB/100 pH4.0.
B) 1 mg of Bis-Tris coupled magnetic polystyrene beads washed with 1 ml of PB/100, followed by treatment with 0.1% Polyacrylic acid (PA, 240,000 M.Wt, w/w) for 5 minutes. The beads were then washed with 1 ml PB1/100 pH4.0, and then treated with 200 µl of 1 mg/ml Poly Tris (PT) and incubated for 5 minutes at room temperature. The beads were washed with 1 ml of PB/100 pH4.0.

Eight replicate samples of the above bead types were prepared for the experiment, with four of each type used to bind Insulin and four used as background controls. After incubation, the bead samples were drawn to a magnet, the supernatant removed and the beads resuspended in 1 ml of PB/100 buffer. The samples were then resuspended and eluted with 200 µl of elution buffer (EB), and after removal of the supernatant, a second elution performed with 200 µl of Sodium Hydroxide (10 mM). Insulin yields were calculated from a standard curve of Insulin solutions in Elution Buffer at pH8 using the absorbance at 255 nm. Background measurements taken from the beads without Insulin bound were subtracted from the results.

The mean first elution Insulin yields were:
(A) Bis-Tris: 3 µg/mg+/−1,
(B) Bis-Tris/PA/PT: 38 µg/mg+/−3.

The second elution yields of Insulin were:
(A) Bis-Tris: 16 µg/mg+/−5 µg/mg,
(B) Bis-Tris/PA/PT: 62 µg/mg+/−12

Significantly greater yield of insulin from these beads is obtained by applying one layer each of Polyacrylic acid and Poly Tris polymers compared to the bead alone.

Example 27

Caffeine Binding and Elution

Caffeine is a basic purine, and a bioactive agent which acts as a stimulant to the central nervous system (CNS). Caffeine is a representative member of the group of drugs and other pharmacological and bioactive agents of importance to the medicine and the pharmaceutical, food and beverage industries.

Caffeine (CAF) binding and release was carried out by exposing 1 mg of each of four types of treated bead to 1 ml of 5 mg/ml Caffeine 2 sulfate in PB1/100 pH4.0. These were:
A) 1 mg of Bis-Tris coupled magnetic polystyrene bead washed with 1 ml of PB/100 pH4.0.
B) 1 mg of Bis-Tris coupled beads washed with 1 ml of PB/100 pH 4.0 and treated with 1 ml of 0.5% Polyacrylic acid (240,000 m.wt.) in PB/100 pH4.0 for one hour. Brought onto magnet, then resuspended and washed with 0.75 ml of PB/100 pH4.0 for one hour.
C) 1 mg of Bis-Tris coupled beads washed with 1 ml of PB/100 pH 4.0 and treated with 1 ml of 0.5% Polyacrylic acid (240,000 m.wt.) in PB/100 pH4.0 for one hour. Brought onto magnet, then resuspended and incubated in 0.75 ml of PB/100 pH4.0, for one hour. Then treated with 0.2 mg/ml PolyBis-Tris in 1 ml of PB/100 pH4.0 for 30 minutes. Then washed with 1 ml PB/100 pH4.0. Resuspended in 1 ml of PB/100 pH4.0.
D) 1 mg of Bis-Tris coupled beads washed with 1 ml of PB/100 pH 4.0 and treated with 1 ml of 0.5% Polyacrylic acid (240,000 m.wt.) in PB/100 pH4.0 for one hour. Brought onto magnet, then resuspended and incubated in 0.75 ml of PB/100 pH4.0, for one hour. Then treated with 0.2 mg/ml PolyBis-Tris in 1 ml of PB/100 pH4.0 for 30 minutes. Then washed with 1 ml PB/100 pH4.0. Then incubated in a second amount of Polyacrylic acid (0.5% w/w) in PB/100 pH4.0. Finally washed with 1 ml of PB/100 PH4.0 and resuspended in 1 ml of PB/100 pH4.0.

Four replicate samples of each of the above bead types were prepared for the experiment and used to bind Caffeine. After incubation for 4 hours, the bead samples were drawn to a magnet, the supernatant removed and the beads resuspended in 1 ml of PB/100 buffer twice. The wash was removed, and the samples eluted with 200 µl of elution buffer (EB), and after removal of the supernatant, a second elution performed with 200 µl of Sodium Hydroxide (10 mM). Caffeine yields were calculated from a standard curve of Caffeine solutions in deionised water using the absorbance at 255 nm.

The mean first elution Caffeine yields were:
(A) Bis-Tris: 7.7 µg/mg+/−0.3 se,
(B) Bis-Tris/PA: 23.7 µg/mg+/−0.7,
(C) Bis-Tris/PA/PT: 8.6 µg/mg+/−0.4,
(D) Bis-Tris/PA/PT/PA: 15.2 µg/mg+/−0.5 µg/mg.

On first elution, in this instance, the Polyacrylic layered bead Type B (Bis-Tris/PA) provides a greater yield than the multilayered Type D (Bis-Tris/PA/PT/PA) bead. However the mean second elution yields were:
(A) Bis-Tris: 5.3 µg/mg+/−0.3,
(B) Bis-Tris/PA: 12.4 µg/mg+/−0.3,
(C) Bis-Tris/PA/PT: 9.4 µg/mg+/−0.2,
(D) Bis-Tris/PA/PT/PA: 51.8 µg/mg+/−9.6 µg/mg.

This provides total Caffeine yields of: (A) 13.0 (0.6), (B) 36.1 (0.4), (C) 18.0 (0.5) and (D) 67.0 (10.0) µg/mg. Thus, significantly greater total yield of Caffeine from these beads is obtained by applying one layer each of Polyacrylic acid and Poly Tris polymers compared to the bead covered in Polyacrylic acid polymer alone.

Example 28

Binding and Release of Magnetite

Magnetite is a paramagnetic inorganic iron oxide, and a relatively inert member of the group of natural and synthetic colloids, dispersions and fines important in various industries including biotechnology, environmental management and chemical engineering. This example uses a physical method to distinguish particles that differ in size and charge to conduct an experiment where oppositely charged polymers are pre-adsorbed to the beads. One set is magnetic and can be removed, whilst the other is not but is larger, thus they can be identified and their behaviour with and without adsorbed polymer can be determined.

Colloidal Magnetite (MAG), binding and release was carried out by exposing two types of magnetite to two types of Polystyrene (S7) PB1/100 pH4.0. The two types of Magnetite were:

A) MAG: 1 ml of stock Magnetite (PC170503) was resuspended and washed in 1 ml PB/100 pH3.97. Then 200 µl was diluted in 0.8 ml of PB/100 pH4.0. Further washed and brought up to 1 ml in PB/100 pH4.0. Final size 129.0+/−38.7 and charge +38.1+/−1.2 mV, as measured by Malvern Zetasizer in PB.100 pH4.0.

B) MAG/PA: 1 ml of stock Magnetite(PC170503) washed in 1 ml PB/100 pH3.97 and 200 µl diluted in 0.8 ml of PB/100 pH4.0. This was resuspended in 1 ml of 1% Polyacrylic acid (240,000 mwt) in PB/100 pH4.0 for one hour. Brought onto magnet, then resuspended and incubated with 1 ml of PB/100 pH4.0 for one hour. Final Size 336.8+/−25.4 and −21.8+/−1.0 mV charge.

The 2 types of Polystyrene bead (S7) were:

C) PS: 100 µl of S7 stock (c. 10% w/w) placed into 0.9 ml of PB/100 pH 4.0. Size 186.4+/−2.5 nm, and −40.6+/−0.9 mV charge.

D) PS/PT: 100 µl of S7 stock (c. 10% w/w) placed into 0.9 ml of PB/100 pH 4.0. Centrifuged at 13,000 rpm for 10 minutes and resuspended in 100 µl PB/100 and incubated in 0.9 ml PolyBis-Tris (0.2% w/w) in PB/100 pH4.0. Washed with 1 ml of PB/100 PH4.0 and resuspended in 1 ml of PB/100 pH4.0. Size 370+/−31 nm, and +33.3+/−2.0 mV charge.

Three replicate samples of each of the above bead types were prepared for the experiment. The experiment comprised adding equal volumes (200 µl) of Type C (PS), to Magnetite Type A (MAG) and Type D (PS/PT) to Type B (MAG/PA). The three replicates of each of the two experiments was then treated in one of the following ways:

I) One set of the replicates was kept for size analysis as combined; either C with A (PS-MAG) and D with B (PSPT-MAGPA).

II) A second set, as (I) above, was treated with 600 µl of Elution Buffer (EB). The magnetic proportion of the bead samples were then drawn to a magnet, the supernatant removed (with any unbound Polystyrene (PS) beads), saved for size measurement, and the magnet captured material resuspended in 0.5 ml of PB/100 buffer pH4.0, also saved for PCS size measurement.

III) A third set, as (I) above, was treated with 600 µl of Sodium Hydroxide (10 mM, EB2).

The mean size of four measurements were:
(1) PS-MAG: 264+/−9.8 nm,
(2) PSPT-MAGPA: 412.6+/−18 nm,
(3) PS-MAG First Elution (EB1 pH8) Resuspend from Magnet: 330+/−16 nm,
(4) PS-MAG First Elution (EB1) Not Drawn to Magnet: 43.5+/−37 nm (i.e. clear),
(5) PSPT-MAGPA First Elution (EB1) Resuspend from Magnet: 199.1+/−90 nm,
(6) PSPT-MAGPA First Elution (EB1) Not Drawn to Magnet: 238.7+/−50 nm,
(7) PS-MAG Second Elution (EB2 pH11) Resuspend from Magnet: 272.7+/−25 nm,
(8) PS-MAG Second Elution (EB2) Not Drawn to Magnet: 240.6+/−20 nm,
(9) PSPT-MAGPA Second Elution (EB2) Resuspend from Magnet: 120.3+/−66 nm,
(10) PSPT-MAGPA Second Elution (EB2) Not Drawn to Magnet: 229.7+/−27 nm.

These results are depicted in FIG. 12.

The difference in nominal size and paramagnetic response allows separation of the these particles as they are aggregated and dispersed, through either of two routes: (1) through their inherent charge or (2) that laid down by polyion adsorption to oppositely charged particles. The example here compares naked oppositely charged particles and their aggregation behaviour, compared to similar particles brought together when bearing oppositely charged polymer layers. PS-MAG (1) gives an aggregation (264 nm) bigger than either particle alone, MAG 129 nm and PS 186 nm. Similarly, adsorption of. polymers increases the size of MAGPA to 337 nm and PSPT 370 nm, with a MAGPA-PSPT aggregation size of 413 nm. On first elution PS-MAG is all cleared to a magnet 330 nm (3), as there are no beads in the supernatant 43 nm (4). PSPT-MAGPA on first elution comprises 199 nm (5) to the magnet and 238 nm (6) in the supernatant, there is a differential in sizes, with the supernatant enhanced in larger (non-magnetic) PS based particles. Under second elution (EB2) PS-MAG shows larger material aggregated on the magnet 273 nm and smaller material 240 nm suspended, indicating some release of PS particles, but the aggregate resuspended from the magnet showing no difference in size to the initial PS-MAG aggregate of 264 nm (1). By comparison, the PSPT-MAG under second elution, shows regeneration of the original magnetite as particles of 120 nm (9) resuspended from the magnet, whilst the supernatant has size 230 nm (10), which is within 44 nanometres of unbound PS bead at 186 nm. Thus, in this example, we have demonstrated that the dual polyion layer (albeit placed on different surfaces initially—temporal ordering) has enabled contact adhesion between particles, and their detachment and separation by physicochemical means (change in pH), which similar particles with surfaces bearing opposite charge but no polyion structure cannot achieve.

Example 29

Filter Paper Loading of PolyIon Layers

In this example, calf thymus DNA binding and release was carried out on two types of filter paper used as porous support materials bearing four pretreatments with polyion solutions. Whatman Number 2 (W2)and 54 (W54) filter papers were treated with either Polyacrylic acid and/or Polybis-tris before being treated with to 3 ml of 50 µg/ml Calf thymus DNA in PB1/100 pH4.0.

Four sets of four replicates of 30×47 mm (c14 cm2) for both Whatman filter papers 2 & 54 were prepared with the following treatments:

A) PT: 1 ml of 1 mg/ml Polybis-tris in PB/50 pH4.0, incubated for 10 minutes, and then drained.

B) PT/PA: 1 ml of 1 mg/ml Polybis-tris in PB/50 pH4.0, incubated for 10 minutes, and then drained. Then 1 ml of 0.5%. (w/v) Polyacrylic acid (240 k M.wt), rotated for 30 minutes and drained.

C) PA: 1 ml of 0.5% (w/v) Polyacrylic acid (240 k M.wt) in PB/50 pH4.0, incubated for 10 minutes, and then drained.

D) PA/PT: 1 ml of 0.5% (w/v) Polyacrylic acid (240 k M.wt), in PB/50 pH4.0, incubated for 10 minutes, and then drained. Then incubated in 1 ml of 1 mg/ml PolyBis-Tris in PB/50 pH4. rotated for 30 minutes and drained.

A single wash of 5 ml of PB/100 is added to each treatment. Then 1 ml of 50 µg/ml calf thymus DNA in PB/100 pH4.0 is incubated for 5 minutes, followed by 2 washes of 3 mls of PB/50 pH4.0. Elution is carried out with 2 mls of Elution Buffer (EB) with the following results:

(A) WhatmanNo.2 (W2), PT: 0.30 µg/cm2+/−0.05,
(B) W2, PT/PA: 0.85 µg/cm2+/−0.09,
(C) W2, PA: 0.41 µg/cm2+/−0.01,
(D) W2, PA/PT: 0.89 µg/cm2+/−0.12,
(E) WhatmanNo. 54(W54), PT: 0.41 µg/cm2+/−0.02,
(F) W54, PT/PA: 0.8 µg/cm2+/−0.10,
(G) W54,PA: 0.47 µg/cm2+/−0.01,
(H) W54,PA/PT: 0.82 µg/cm2+/−0.00.

This shows that filter paper is acting as a reservoir for the solution reacted material, since the paper was not allowed to dry between treatments, and consequently, there is no ordering effect between PT/PA or PA/PT, supported in the filter paper in its ability to bind or release of DNA. However, it also shows that PA to PT or PT to PA has a significant advantage over PolyBis-Tris when applied alone to the filter papers.

Example 30

Sub-Micron Non-Magnetic Multilayered Particle Containing DNA

Nanoparticle and microparticulate polymer systems below 1000 nm (1 micron) in size have characteristic roles as carriers, components, and adhesive systems in materials, paints, coatings and colloidal dispersions. Such particles have wide ranging application in the fields of medicine, pharmaceuticals, food, chemical industries, cosmetics, agrochemicals, electronics, aerospace and defence, and emerging nanotechnology and biotechnology industries.

This example uses a polystyrene microparticle that serves as submicron cores onto which many multilayers of alternately charged polymers are progressively laminated. The polymer layers are deposited between extensive clean-up cycles that require centrifugation in order to replace the supernatant contaminated with excess polymer. A core carboxylated particle designated D-S6 (149 nm+/−1.2 and charge −53.9+/−1.6) was used. 2×1 ml of starting material of each bead stock (5% wt fraction) was cleaned up by 5 successive centrifugation cycles (13,000 rpm 30 minutes), with supernatant removal and resuspension using 1 ml volumes of 18 MegaOhm MilliQ water, yielding approximately 50 mg/ml for each experimental particle set.

Onto this core the following layers were constructed:

Layer 1—Polycation: 100 µl (c5 mg) of Core Bead was spun down, supernatant removed, and incubated with 1 ml of 2 mg/ml PolyBis-Tris (15 k) in water to provide a first layer of polycation for 30 minutes. Wash twice with centrifugation 13,000×15 mins.

Optional Layer 2—DNA: An optional DNA binding step, for one replicate, with 1.4 ml of genomic calf thymus DNA at 500 µg/ml in PB/100 pH4.0 RT for 30 minutes, wash twice.

Layer 2—Polyanion: Beads resuspended in 100 µl of PB/100 pH4.0, then add 1 ml of 0.5% (w/v) 240,000 M.wt Polyacrylic Acid in PB/100 pH4.0. Spin at 13,000 rpm and resuspend twice in PB/100.

Layer 3—Polycation: Treat with second 1 ml of 2 mg/ml 15K PolyBis-Tris for 10 minutes. Repeat two cycles of centrifugation with PB/100 to wash.

Layer 4—DNA: DNA binding step with 1.4 ml of genomic Calf thymus DNA at 500 µg/ml in PB/100 pH4.0 RT for 30 minutes, wash twice.

Layer 5—Polyanion: Use Polyacrylic Acid 15,000 0.5% w/v in deionised water 10 minutes, wash twice.

Layer 5—Polycation: PolyBis-Tris as per layer 3, but over the DNA layer 4.

Layer 6—Polycation: PolyBis-Tris as per layer 3, but over Polyacrylic Layer 5.

The experiment was designed with 9 starting tubes containing the core bead type. A series of tubes was thus obtained containing D-S6 Core, Core/PT, Core/PT/DNA, Core/PT/PA, Core/PT/PA/PT, Core/PT/PA/PT/DNA, Core/PT/PA/PT/DNA/PA, Core/PT/PA/PT/DNA/PT, Core/PT/PA/PT/DNA/PA/PT.

These beads were then analysed for surface charge (zeta potential) in PB/100 at pH4.0 and for those containing DNA, single measurements of elution of DNA with standard EB elution buffer at pH 8.0 using 200 µl of 1000 µl sample (c1 mg). The results for bead D-S6 were:

(1) S6: −37.8 mV+/−18.50
(2) S6/PT: +34.9 mV+/−1.3
(3) S6/PT/DNA: 32.3 mV+/−2.5, EB1 elutes 30.0 µgDNA.
(4) S6/PT/PA: −23.9 mV+/−2.6
(5) S6/PT/PA/PT: 25.5 mV+/−1.0
(6) S6/PT/PA/PT/DNA: 28.0 mV+/−1.3, EB1 elutes 33.84 µgDNA
(7) S6/PT/PA/PT/DNA/PA: −27.5 mV+/−5.1, EB1 elutes 21.2 µgDNA
(8) S6/PT/PA/PT/DNA/PT: 28.5 mV+/−5.0, EB1 elutes 29.3 µgDNA
(9) S6/PT/PA/PT/DNA/PA/PT: 33.7 mV+/−0.8, EB1 elutes 16.3 µgDNA.

These results show that alternate multilayering with polycation or polyanion causes a change in polarity of the charge that the beads carry. In addition, embedded layers of DNA are incorporated whilst the surface charge of the bead is changed after the DNA deposition, as evidenced by release of DNA by elution from these beads after the surface charge has been modified by subsequent polyion layers, e.g. 8.C/PT/PA/PT/DNA/PA. Thus, in a general way, the present invention allows DNA to be interlayered within alternating polyion layers.

Example 31

Effect of an Outer Layer of Polycation on Multilayer Stability

A similar experiment to Example 30 was performed with 10 different carboxylated polystyrene bead types were coated to the four layers Core/PAM/PA/PT/DNA (Layer 4) and a group with a further outer layer of PolyBis-Tris (Layer 5) Core/PAM/PA/PT/DNA/PT. The first layer applied was Polyallylamine 15,000 (0.05% w/v m.wt). The mobility and elution of DNA was followed with agarose gel electrophoresis and absorbance at 260/280 nm.

Agarose gel results show that all the 4 and 5 layer beads bind DNA (FIG. 13). Analysis of the first and second elutions show that there is no statistically significant difference in either the release of DNA from the four layer preparation (Yield µg +/−) and five layer preparations or the surface charge between those layers. However, there is a weak correlation between the scale of elution of DNA from a 5 layer bead, with an over layer of PolyBis-Tris, that depends on the scale of elution of DNA from the 4 layer DNA bead beneath. We also found that in the elution of DNA from 4 and 5 layer beads, a PolyBis-Tris outer layer reduces release compared to DNA only adsorbed to a PolyBis-Tris substrate. Thus, DNA sandwiched between two PolyBis-Tris layers is stabilized, with first elution reduced and shifted to second elution, as it shows approximately 20% reduced first elution (Slope m=0.8, pH8, r=0.713, df=8, $r_{stat}$=0.685, P=0.02, Significant at 2% level of probability) and a concomitant 20% greater second elution (Slope L5 on L4 m=1.2, pH11, r=0.889 df=7 $r_{stat}$=0.798, P=0.01, Significant at 1% level of probability) than an 4 layer system with adsorbed DNA (Layer 4) exposed on the surface.

Example 32

Preparation of Colloidal PolyBis-Tris and Polyacrylic Acid Polyion Polyion Complex Colloids Containing GFP Plasmid Polyion complexes are representative of materials used in diverse applications, from colloidal dispersions used in advanced formulations for the delivery of drugs and therapeutics, through to materials with activated and functional surfaces used in special composites such as membranes in separation technology applications. Polyion complexes as dispersions or solid phases are thus a representative type of materials used in many industries, including biotechnology, biomedical, and pharmaceutical fields.

Dispersions of PolyBis-Tris complexed with Polyacrylic acid were formulated by simple addition of one of two molecular weights of PolyBis-Tris solution with one of two molecular weights of Polyacrylic acid solution. The solutions were:

(A) Polyacrylic Acid (PA15 15,000 molecular weight solution 0.1% w/v in PB/50 pH4.60, (−7.1 mV+/−11.7),
(B) Polyacrylic Acid (PA240), 240,000 molecular weight solution 0.1% w/v in PB/50 pH43.75 (−1.7 mV+/−5.7),
(C) PolyBis-Tris (PT15) 15,000 molecular weight solution 0.1% w/v in PB/50 pH4.46(+5.4 mV+/−3.9),
(D) Polyacrylic Acid (PT240) 240,000 molecular weight solution 0.1% w/v in PB/50 pH4.82(+3.6 mV+/−0.6).

Equal volumes of solutions were added to produce polyion dispersions. Complexes from solution combinations of (1) A to C, A to (2) D and (3) B to C, (4) B to D were made. The direction of addition was reversed for a second group with (5) C to A, (6) C to B and (7) D to A, (8) D to B. The resulting formulations were analysed for size and charge in PB/100 at pH4.0:

| Type PA to PT | Zeta (mV) | se | Size (nm) | se |
|---|---|---|---|---|
| 1. PT15-PA15 | 4.1 | 1.7 | 95 | 75 |
| 2. PT240-PA15 | 17.7 | 1.8 | 182 | 23 |
| 3. PT15-PA240 | 3.5 | 0.4 | 142 | 98 |
| 4. PT240-PA240 | 3.6 | 1.6 | 136 | 62 |
| 5. PA15-PT15 | 25.6 | 1.2 | 112 | 173 |
| 6. PA240-PT15 | 30.9 | 0.5 | 346 | 11 |
| 7. PA15-PT240 | 7.6 | 3.4 | 82 | 67 |
| 8. PA240-PT240 | 21.0 | 1.3 | 724 | 527 |

Differences in size and charge occur from the direction of mixing. To some of these dispersions were added a further treatment of PolyBis-Tris PT240 0.5 mg/ml PB/200 pH4.0 with the following results:

| Type PT-PA-PT | Zeta (mV) | se | Size | se |
|---|---|---|---|---|
| PT15-PA15-PT240 | 2.8 | 1.1 | 122 | 49 |
| PT240-PA15-PT240 | 2.7 | 1.0 | 112.2 | 86 |
| PT15-PA240-PT240 | 3.4 | 0.9 | 69 | 80 |

Charge modification of the surface layer indicates that the outermost layer of the dual polymer formulations can be changed by adsorption of a third polymer treatment. Some of these formulation types were used to bind GFP Plasmid (5.1 kb, pCS2*mt-SGP). They were:

(1) PT15 (PL)-PA15: GFP plasmid (1 µg of endotoxin free plasmid in 30 ul DW) was added to 1 ml of 0.2% PT 15 k in PB/100 and incubated for 10 minutes. To this 2 mls of 0.1% PA 15 k in PB/100 was added, twice washed by centrifugation and resuspension in PB/100, and finally resuspended in 60 µl of PB/100 pH4.0.

(2) PT15 (PL)-PA15-PT15: GFP plasmid (1 µg of endotoxin free plasmid in 30 ul DW) was added to 1 ml of 0.2% PT 15 k in PB/100 and incubated for 10 minutes.). To this 2 mls of 0.1% PA 15 k in PB/100 was added, twice washed by centrifugation and resuspension in PB/100 and finally resuspended in 1000 µl of PB/100 pH4.0. Then 1 ml of 0.2% PT15 k was added, then washed twice and resuspended in 60 µl EB/100.

(3) PT240 (PL)-PA15: GFP plasmid (1 µg of endotoxin free plasmid in 30 ul DW) was added to 1 ml of 0.2% PT 240 k in PB/100 and incubated for 10 minutes. To this 2 mls of 0.1% PA 15 k in PB/100 was added, twice washed by centrifugation and resuspension in PB/100, and finally resuspended in 60 µl of PB/100 pH4.0.

4) PT240 (PL)-PA15-PT240: GFP plasmid (1 µg of endotoxin free plasmid in 30 ul DW) was added to 1 ml of 0.2% PT 240 k in PB/100 and incubated for 10 minutes. To this 2 mls of 0.1% PA 15 k in PB/100 was added, twice washed by centrifugation and resuspension in PB/100, and finally resuspended in 1000 µl of PB/100 pH4.0. Then 1 ml of 0.2% PT240 k was added, then washed twice and resuspended in 60 µl EB/100.

5) PT15 (PL)-PA240: GFP plasmid (1 µg of endotoxin free plasmid in 30 ul DW) was added to 1 ml of 0.2% PT 15 k in PB/100 and incubated for 10 minutes. To this 80 µl of 0.5% PA 240 k in PB/100 was added, twice washed by centrifugation and resuspension in PB/100, and finally resuspended in 60 µl of PB/100 pH4.0.

6) PT15 (PL)-PA240-PT15: GFP plasmid (1 µg of endotoxin free plasmid in 30 ul DW) was added to 1 ml of 0.2% PT 15 k in PB/100 and incubated for 10 minutes. To this 80 µl of 0.5% PA 240 k in PB/100 was added, twice washed by centrifugation and resuspension in PB/100, and finally resuspended in 1000 µl of PB/100 pH4.0. Then 40 µl of 2% PT15 k was added, then washed twice and resuspended in 60 µl EB/100.

The presence of GFP plasmid in the formulations was tested with 6 µl samples on a 1% agarose electrophoresis gel, without elution. This is shown in FIG. 14 with Samples 1 through 6 labelled as lanes 3, 4, 5, 6, 13 & 14 on the gel respectively. Examples (1) PT15 (PL)-PA15 (Lane 3), (2) PT15(PL)-PA15-PT15 (Lane 4), (3) PT240 (PL)-PA15 (Lane 5) and (6) PT15 (PL)-PA240-PT15 (Lane 14) all contain plasmid, whilst the loads released under electrophoresis for (4) PT240 (PL)-PA15-PT240 and (5) PT15 (PL)-PA240 (Lane 13) were the smallest.

Example 33

Tranfection of Mammalian COS Cells with Polyion Formulations Containing GFP Plasmid Polyion formulations incorporating GFP, a plasmid incorporating a gene coding green fluorescent protein, are useful as markers in the science and technology of transfection, gene modification of plants and animals and gene therapy of diseases. Such preparations are representative of the class of formulations used in the pharmaceutical, biotechnology, bioscience, medicine and gene modification industries.

Experiments were performed to transfect mammalian COS cells with different types of polyion complex containing the GFP plasmid. Particle types used include those from Example 29, sub-micron multi layered particles based on a core bead, and Example 30, disperse formulations of Poly-Tris and Polyacrylic acid, and were formulated to contain GFP plasmid.

The first type were based on core polystyrene types S5 and S6. The following layers were prepared: $S5/PT_{240}[PL]/PA_{15}/PT_{240}$ and stocks of $S5/PT_{240}/PA_{15}/PT_{240}$ and $S6/PT240/PA15/PT240$ from which $S5/PT_{240}/PA_{15}/PT_{240}[PL]/PA_{15}/$, $S5/PT_{240}/PA_{15}/PT_{240}[PL]PT_{240}$, $S5/PT_{240}/PA_{15}/PT_{240}[PL]/PA_{15}/PAM$, $S5/PT_{240}/PA_{15}/PT_{240}[PL]/PAM$; $S6/PT_{240}/PA_{15}/PT_{240}[PL]/PT_{240}$ and $S6/PT_{240}/PA_{15}/PT_{240}[PL]/PAM$ were formulated.

The second type of dispersion-formed particles prepared were $PT_{15}[PL]PA_{15}$, $PT_{15}[PL]PA_{15}/PT_{15}$, $PT_{240}[PL]PA_{15}$, $PT_{240}[PL]PA_{15}/PT_{15}$, $PT_{15}[PL]PA_{240}$, $PT_{15}[PL]PA_{240}/PT_{15}$.

Controls, without polyion layers, were prepared of $PT_{240}[PL]$, $PT_{15}[PL]$ and $PT_{240}$ alone, and the S5 & S6 sets: $S5/PT_{240}[PL]$ and $S6/PT_{240}[PL]$ as non-layered controls. Samples containing nominal 1 µg of GFP plasmid were suspended in 60l of PB/100. The samples were presented to COS-7 cells using the method given below, and results assessed for green fluorescence as evidence of transfection using a confocal microscope.

Transfection Methodology:

COS 7 cells were cultured to confluence in D-MEM containing 10% foetal calf serum (FCS), L-glutamine and penicillin/streptomycin in 75 cm2 tissue culture flasks. Cells were trypsinised for 1 to 2 min at 37° C. and, following neutralisation and dilution with media (D-MEM containing 10% FCS and L-glutamine (no antibiotic)) to give an approximate cell density of 2×105/ml, were replated in 300 µL volumes into 8 well chamber slides. Following overnight incubation at 33° C. in an environment of 7% $CO_2$, the volume of media in each well was reduced to 250 µl in preparation for transfection. Transfections were performed directly into cells plus overnight culture media or into cells plus acidified overnight culture media. Culture media was acidified by the addition of 4 µl 100 mM citric acid, which reduces the pH of the media in each well to approximately 7.2. Samples for transfection were prepared as indicated in Table 1. 50 µl of each sample was used to transfect COS 7 cells in 250 µl of overnight culture under standard or acidic conditions. Positive controls utilising lipofectamine (Invitrogen) mediated transfection were prepared as follows. 16 µl GFP plasmid (1 µg/40 µl) was diluted with 9 µl D MEM to give a final volume of 25 µl. In a separate microfuge tube, 1 µl of lipofectamine reagent was diluted with 24 µl D-MEM and, after gentle mixing, was incubated at room temperature for either 3 or 5 min. After incubation, the GFP-D-MEM sample was mixed with the lipofectamine-D-MEM sample. After a further 20-30 minutes incubation at room temperature, 50 µl of the resulting mixture was then used to transfect cells in 250 µl media under standard or acidic conditions. Following addition of all samples, cells were incubated for 24-48 h at 37° C. in an environment of 7% $CO_2$.

Generation of GFP was evaluated by fluorescence and confocal microscopy [Zeiss LSM 510 Meta Confocal Microscope] using an excitation wavelength of 488 nm and GFP fluorescence detected at 520 nm.

Preparation of Samples for Transfection:

| Sample | Vol(µl) DNA sample | Vol (µl) D-MEM |
|---|---|---|
| Test polymer-DNA complexes (designated GFP 1–19) | 25 | 25 |
| PT polymer only (negative control) | 25 | 25 |
| GFP Plasmid only (negative control) | 16 | 9 |
| Lipofectamine reagent only (negative control) | 1 | 24 |

Results: fluorescence confocal photomicrographs were taken of representative regions of the experiment plates. The results are summarized in table form:

GFP FORMULATION TRANSFECTION OF COS-7 CELLS
RESULTS TABLE: EXAMPLE 33

| TYPE | CODE | GFP FLUORESCENCE RANK Low = * (1) High = ****** Standard Conditions | GFP FLUORESCENCE RANK Low: * (1) High = ****** (6) Acid Conditions |
|---|---|---|---|
| PT240 ONLY - Negative Control | GFP20 | * | * |
| PT240[PL] | GFP1 | n/a | n/a |
| PT15[PL]/PA15 | GFP3 | ** | *** |
| PT15[PL]/PA15/PT15 | GFP4 | ** | * |
| PT240[PL]/PA15 | GFP5 | * | * |

-continued

| | | GFP FLUORESCENCE RANK Low = * (1) High = ****** Standard | GFP FLUORESCENCE RANK Low: * (1) High = ****** (6) Acid |
|---|---|---|---|
| TYPE | CODE | Conditions | Conditions |
| PT240[PL]/PA15/PT15 | GFP6 | **** | *** |
| PT15(PL)/PA240 | GFP13 | ** | * |
| PT15(PL)/PA240/PT15 | GFP14 | * | * |
| PT15/PL | GFP15 | * | * |
| S5/PT240[PL] | GFP7 | *** | *** |
| S6/PT240[PL] | GFP2 | * | * |
| S5/PT240[PL]/PA15/PT240 | GFP8 | ** | * |
| S5/PT/PA/PT [PL]/PT240 | GFP10 | * | * |
| S5/PT/PA/PT[PL]/PA15/PT240 | GFP9 | * | * |
| S5/PT/PA/PT[PL]/PA15/PAM | GFP11 | ***** | **** |
| S5/PT240/PA15/PT240[PL]/PAM | GFP12 | ** | ** |
| S5/PT240[PL] (EtOH Clean) | GFP16 | * | * |
| S6/PT15[PL] | GFP17 | * | * |
| S6/PT/PA/PT(PL)-PT240 | GFP18 | * | * |
| S6/PT/PA/PT (PL)-PAM | GFP19 | *** | *** |
| Positive Control - Lipofectamine + GFP | GFP21 | ****** | ****** |
| Negative Control - Lipofectamine only | GFP21 | * | * |
| Negative Control- COS7 Cells | GFP22 | * | * |
| Negative Control-Free GFP Plasmid | GFP23 | * | ** |

Key:
PL = GFP Plasmid
PA = PolyAnion
PT = PolyBisTris
PAM = PolyAMine (S6 Core = 150 nm) (S5 Core = 140 nm)
PT/PA/PT = PT240/PA15/PT240.
Stock Samples contain nominal 1 μg plasmid formulation in approximately 60 μl 6 mM KAcetate.
GFP Fluorescence assessed by microscopy [Zeiss LSM 510 Meta Confocal] Ex 488 nm Em520 nm.

These results showed that negative and positive controls worked effectively, so that GFP tranfection could be detected as green fluorescence in micrographs. GFP formulations with an outer layer of PAM with inner layers of GFP plasmid and PolyBisTris gave significant fluorescence demonstrating that real transfection results were achieved. The relative response was ranked and tabulated and results shown above.

Example 34

DNA Purification Using Polyion Layering on a 96 Pin Plastic Disposable

A set of plastic 96 pins was used obtained from Mimotopes Pty Ltd modified with either amine or carboxy groups on the surface. Some were soaked for 60 minutes in a solution of Poly-BisTris prepared in accordance with WO02/48164 at pH4 or an additional solution of polyacrylic acid (MW 240K) at 5 mg per ml to form an additional layer. After washing away the free polymers with water, the pins were dipped into a solution of bovine DNA at about 100 ug/ml in 15 mM potassium acetate buffer at pH4 and incubated for 60 minutes. The pins were washed again and the DNA eluted in 0.5 ml of 10 mM Tris HCl pH8.5 by soaking for about 10 minutes.

Results:

| Pin type | DNA yield (ug) |
|---|---|
| Carboxy (neg. control) | 0 |
| Carboxy-PolyBisTris | 13 |
| Amine (negative control) | 0 |
| Amine-Polyacrylic-PolyBisTris | 35 |

The results showed a typical Charge Switch reaction where the DNA is recovered at a slightly alkaline pH. Also the multi layered approach demonstrates the benefits of a polyion complex where the binding capacity of the surface is significantly increased.

Example 35

Improved DNA Purification Using Polyions

Tip plugs: A tip plug was made by placing a sintered plastic plug at the bottom of a 1 ml pipette tip. The plug was coated with PolyBis-Tris at 5 mg/ml, Polyacrylic acid at 5 mg/ml and Polyallylamine at 5 mg/ml by sequentially soaking the plug and washing with 10 mM potassium acetate buffer pH4 between each layering stage. The Tip plug was then used to bind *E. coli* cells containing PUC19 plasmid from 1 ml of an overnight culture adjusted to pH 4. The bound cells were recovered by eluting with 1 ml of 10 mM Tris HCl pH8.5. The cells were then pelleted by centrifugation and the plasmid extracted using the DRI Plasmid miniprep kit by pooling the pellets from 5 tip plugs. The result showed that the eluted DNA gave an absorbance of 0.15 at 260 nm and a 260/280 ratio of 1.9 indicating a few ug of pure plasmid was recovered.

Magnetic beads: Some DRI Bis-Tris magnetic beads were treated with Polyacrylic acid and Polyallylamine as described above. About 5 mg of the modified beads were used to bind the cells from 2 ml of *E. coli* broth. The beads showed rapid clearance of the broth and release of cells in Elution Buffer as before. The cells were pelleted and the plasmid purified with the DRI plasmid extraction kit. An absorbance at 260 nm of 0.53 and a ratio of 1.7 indicated the presence of purified plasmid DNA. All references referred to herein are intended to be incorporated by reference in their entirety.

The invention claimed is:

1. A method for delivering a desired substance to a target site, the method comprising:
    (a) contacting a carrier with the substance at a first pH so that the substance binds to the carrier by ionic interaction;
    (b) delivering the carrier to a target site;
    (c) releasing the desired substance from the carrier at a second pH, wherein the carrier and the desired substance together form at least three layers which associate by ionic interaction at the first pH, and
    wherein:
    (1) at least one layer comprises poly Bis-Tris;
    (2) at least one layer comprises polyacrylic acid; and
    (3) at least one layer comprises the desired substance.

2. The method of claim 1, wherein the layers are formed on a solid phase or core particle.

3. The method of claim 2, wherein the solid phase is a magnetizable particle.

4. The method of claim 1, wherein the poly Bis-Tris and the polyacrylic acid are each initially immobilized on a separate population of particles.

5. The method of claim 4, further comprising contacting the separate population of particles so that they aggregate to form a layered carrier.

6. The method of claim 1, wherein at the first pH the carrier comprises at least four layers which associate by ionic interaction.

7. The method of any of the preceding claims claim 1, wherein the layers formed by the carrier and the desired substance together comprise at least two layers of the desired substance.

8. The method of claim 7, wherein the at least two layers of the desired substance are releasable at a different second pH.

9. The method of claim 7 or claim 8, wherein the at least two layers of the desired substance comprise different desired substances.

10. The method of claim 7 or claim 8, wherein the at least two layers of the desired substance comprise the same desired substance.

11. The method of claim 1, wherein the desired substance is selected from the group consisting of a nucleic acid, a pharmaceutically active compound, a protein, a carbohydrate, a growth factor, a hormone, an enzyme, a vaccine, a cell, a cell component, a virus, a fertilizer, a pesticide, an insecticide, a herbicide, a fungicide, a vitamin, a feed supplement, an imaging agent, a dye, a chelating agent, a cosmetic, a paint, a detergent, a lipid, a food supplement and a neutraceutical.

12. The method of claim 10, wherein the desired substance is a negatively charged substance at the first pH.

13. The method of claim 10, wherein the desired substance is a positively charged substance at the first pH.

14. The method of claim 10, wherein the desired substance is a zwitterionic substance at the first pH.

15. The method of claim 1, wherein the carrier has an outer layer disposed over the outermost layer of the desired substance.

16. The method of claim 15, wherein the outer layer comprises a charge switch material or a polyionic polymer.

17. The method of claim 10, wherein the desired substance in at least one layer of the carrier is a nucleic acid.

18. The method of claim 10, wherein the desired substance is a nucleic acid and the method transfects cells with the nucleic acid.

19. The method of claim 1, wherein the second pH is below pH 9.0.

20. A carrier for delivering a desired substance to a target site, said carrier comprising at least four layers which associate by ionic interaction, wherein at least one layer comprises poly Bis-Tris.

21. The carrier according to claim 20, wherein the desired substance is bound to the carrier by ionic interaction.

22. A carrier for delivering a desired substance to a target site, said carrier comprising at least three layers which associate by ionic interaction at a first pH, wherein:
    at least one layer comprises poly Bis-Tris;
    at least one layer comprises polyacrylic acid; and
    at least one layer comprises the desired substance;
    wherein the substance is releasable from the carrier at a second pH at which the charge on the poly Bis-Tris is negative, neutral or less positive.

23. The carrier of claim 22, wherein the layers are formed on a solid phase or a core particle.

24. The carrier of claim 23, wherein the solid phase is a magnetizable particle.

25. The carrier of claim 22, wherein wherein the poly Bis-Tris and the polyionic polyacrylic acid are each initially immobilized on a separate population of particles.

26. The carrier of claim 25, further comprising contacting the separate population of particles so that they aggregate to form a layered carrier.

27. The carrier of claim 22, wherein the carrier comprises at least four layers.

28. The carrier of claim 22, wherein the desired substance is selected from the group consisting of a nucleic acid, a pharmaceutically active compound, a protein, a carbohydrate, a growth factor, a hormone, an enzyme, a vaccine, a cell, a cell component, a virus, a fertilizer, a pesticide, an insecticide, a herbicide, a fungicide, a vitamin, a feed supplement, an imaging agent, a dye, a chelating agent, a cosmetic, a paint, a detergent, a lipid, a food supplement and a neutraceutical.

29. The carrier of claim 28, wherein the desired substance is a nucleic acid.

30. The carrier of claim 28, wherein the desired substance is a negatively charged substance at the first pH.

31. The carrier of claim 28, wherein the desired substance is a positively charged substance at the first pH.

32. The carrier of claim 28, wherein the desired substance is a zwitterionic substance at the first pH.

33. The carrier of claim 22, wherein the carrier has an outer layer disposed over the outermost layer of the desired substance.

34. The carrier of claim 33, wherein the outer layer comprises poly Bis-Tris or a polyacrylic acid.

35. The carrier of claim 34, wherein the outer layer of the carrier comprises poly Bis-Tris.

36. The carrier of according to claim 22, wherein the second pH is below pH 9.

37. The carrier of claim 22, wherein the poly Bis-Tris is a polycation at the first pH.

38. The carrier of claim 22, wherein at the first pH at least two layers of the carrier comprise polyacrylic acid.

39. Use of a carrier according to any one of claims 20 to 38 for delivering a desired substance to a target site, the use comprising providing the carrier to the target site wherein the target site is at the second pH.

40. The use of claim 39, wherein the target site is in vivo.

41. The use of claim 39, wherein the desired substance is non-therapeutic.

42. The use of claim 39, wherein the target site is in a plant or an animal.

43. A carrier according to any one of claims 20 to 38 for use in a method of treatment of the human or animal body with a desired substance, wherein the carrier is for delivering the desired substance to an intracellular target site at the second pH to release the desired substance.

44. A method of isolating desired substance from a sample, the method comprising: at a first pH, bringing the sample into contact with the carrier of any one of claims 20 to 38, such that the desired substance is bound to the carrier; and releasing the desired substance at a second, higher pH at which the charge on the material is negative, neutral or less positive.

* * * * *